US012714302B2

(12) United States Patent
Duncan et al.

(10) Patent No.: US 12,714,302 B2
(45) Date of Patent: Aug. 25, 2026

(54) ELECTRODE SYSTEM FOR VISION TREATMENT AND METHOD

(71) Applicant: i-Lumen Scientific, Inc., Bloomington, MN (US)

(72) Inventors: Thu-Ha Duncan, Cleveland, TN (US); John C. Velure, Minnetonka, MN (US); Marshall T. Masko, Minnetonka, MN (US)

(73) Assignee: i-Lumen Scientific, Inc., Bloomington, MN (US)

( * ) Notice: Subject to any disclaimer, the term of this patent is extended or adjusted under 35 U.S.C. 154(b) by 880 days.

(21) Appl. No.: 17/924,852

(22) PCT Filed: May 11, 2021

(86) PCT No.: PCT/US2021/031869
§ 371 (c)(1),
(2) Date: Nov. 11, 2022

(87) PCT Pub. No.: WO2021/231496
PCT Pub. Date: Nov. 18, 2021

(65) Prior Publication Data
US 2023/0181028 A1 Jun. 15, 2023

Related U.S. Application Data

(60) Provisional application No. 63/025,987, filed on May 15, 2020.

(51) Int. Cl.
*A61N 1/36* (2006.01)
*A61B 3/028* (2006.01)
*A61N 1/04* (2006.01)

(52) U.S. Cl.
CPC ............ *A61B 3/028* (2013.01); *A61N 1/0476* (2013.01); *A61N 1/36031* (2017.08); *A61N 1/36046* (2013.01)

(58) Field of Classification Search
CPC .. A61B 3/028; A61N 1/0476; A61N 1/36031; A61N 1/36046; A61N 1/0496;
(Continued)

(56) References Cited

U.S. PATENT DOCUMENTS 3,669,119 A * 6/1972 Symmes .............. A61N 1/0408 600/26
5,522,864 A 6/1996 Wallace et al.
(Continued)

FOREIGN PATENT DOCUMENTS

JP H04244171 A 9/1992
JP 2000116797 A 4/2000
(Continued)

OTHER PUBLICATIONS

Sehic, A., et al., Electrical Stimulation as a Means for Improving Vision, The American Journal of Pathology, vol. 186, No. 11, Nov. 2016, pp. 2784-2797.
(Continued)

*Primary Examiner* — Eugene T Wu
(74) *Attorney, Agent, or Firm* — Fox Rothschild LLP

(57) ABSTRACT

A system and method for electrical stimulation of the human body, and in particular, to systems and methods for electrode systems and signal delivery used in electrical-stimulation treatment, testing and monitoring of vision problems of a patient, analyzing the results of the treatments, and monitoring to determine, for example, whether a medical treatment for the patient needs to be continued and/or altered, wherein the design and placement of the electrode systems and adjustment of signals delivered to the electrodes facilitate adjustment of the geometry of signal flow through the tissues of the patient.

21 Claims, 20 Drawing Sheets

(58) Field of Classification Search
CPC .. A61N 1/3756; A61N 1/0456; A61N 1/0492; A61N 1/375
See application file for complete search history.

(56) References Cited

U.S. PATENT DOCUMENTS

| | | | |
|---|---|---|---|
| 6,019,877 | A | 2/2000 | Dupelle |
| 6,035,236 | A | 3/2000 | Jarding et al. |
| 6,275,735 | B1 | 8/2001 | Jarding et al. |
| 6,385,727 | B1 | 5/2002 | Cassagnol et al. |
| 6,736,511 | B2 | 5/2004 | Plummer et al. |
| 7,251,528 | B2 | 7/2007 | Harold |
| 8,048,068 | B2 | 11/2011 | Falkenstein et al. |
| 8,888,288 | B2 | 11/2014 | Iravani et al. |
| 9,237,842 | B2 | 1/2016 | Lee et al. |
| 9,283,371 | B2 | 3/2016 | Duncan |
| 9,839,352 | B2 | 12/2017 | Wallace et al. |
| 10,299,674 | B2 | 5/2019 | Correns et al. |
| 10,391,312 | B2 | 8/2019 | Mowery et al. |
| 10,780,273 | B2 | 9/2020 | Franke et al. |
| 10,799,114 | B2 | 10/2020 | Marquez et al. |
| 10,842,373 | B2 | 11/2020 | Fink et al. |
| 11,439,823 | B2 | 9/2022 | Masko et al. |
| 2008/0028214 | A1 | 1/2008 | Tafoya et al. |
| 2016/0136434 | A1 | 5/2016 | Lee et al. |
| 2017/0188811 | A1 | 7/2017 | Lee |
| 2017/0266446 | A1 | 9/2017 | O'Clock |
| 2018/0318586 | A1 | 11/2018 | Salazar |
| 2019/0143116 | A1* | 5/2019 | Mowery ............ A61N 1/36014 607/53 |
| 2019/0374775 | A1 | 12/2019 | Mowery et al. |
| 2020/0391029 | A1 | 12/2020 | Mullins et al. |
| 2022/0047866 | A1 | 2/2022 | Masko et al. |

FOREIGN PATENT DOCUMENTS

| | | | |
|---|---|---|---|
| JP | 2012235824 | A | 12/2012 |
| JP | 2014008282 | A | 1/2014 |
| JP | 2019510603 | A | 4/2019 |
| WO | 2017048731 | A1 | 3/2017 |
| WO | 2017160912 | A1 | 9/2017 |
| WO | 2020252278 | A1 | 12/2020 |

OTHER PUBLICATIONS

Extended European Search Report for European Application No. 26153569.4, filed Jan. 22, 2006 mailed Feb. 11, 2026.

* cited by examiner

FIG. 1A1
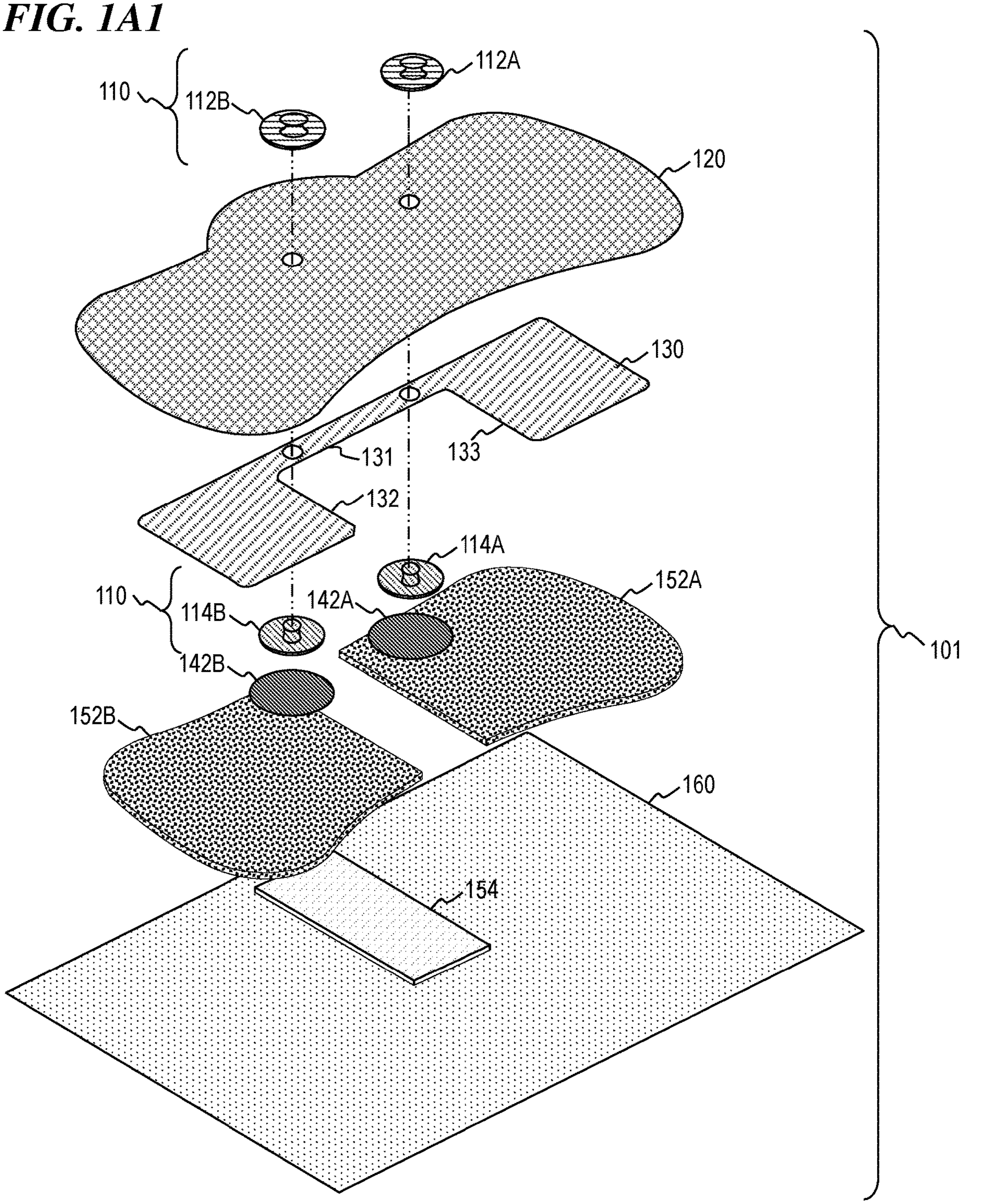

FIG. 1A2
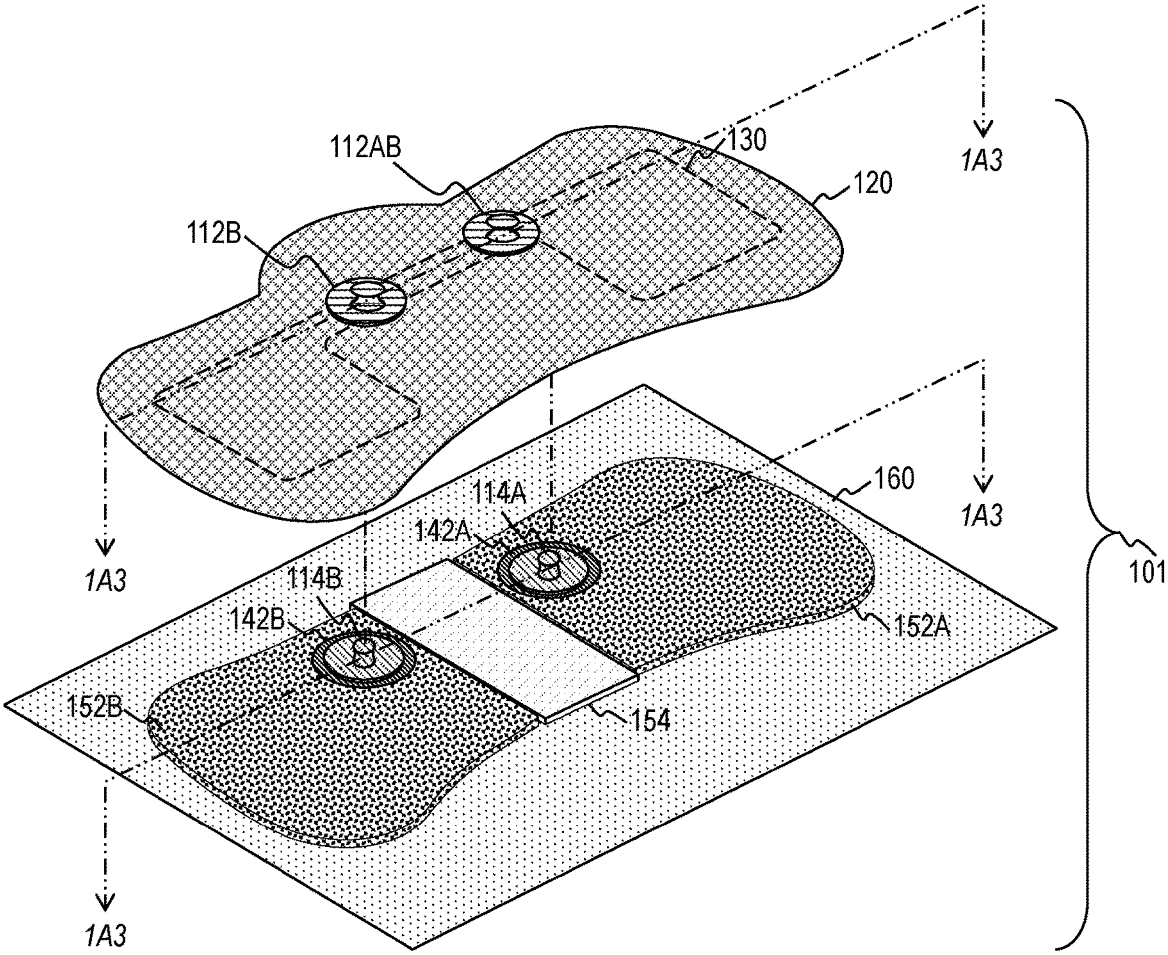
FIG. 1A3
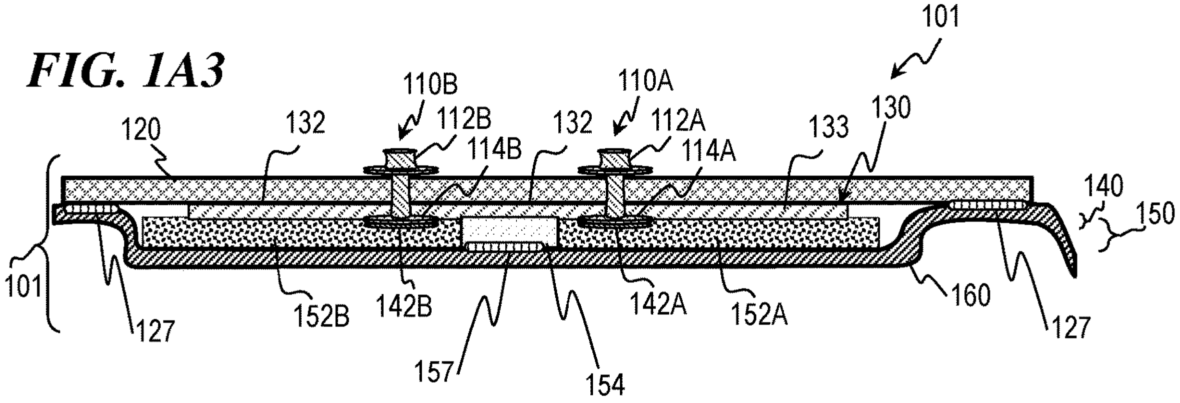

*FIG. 1B1*
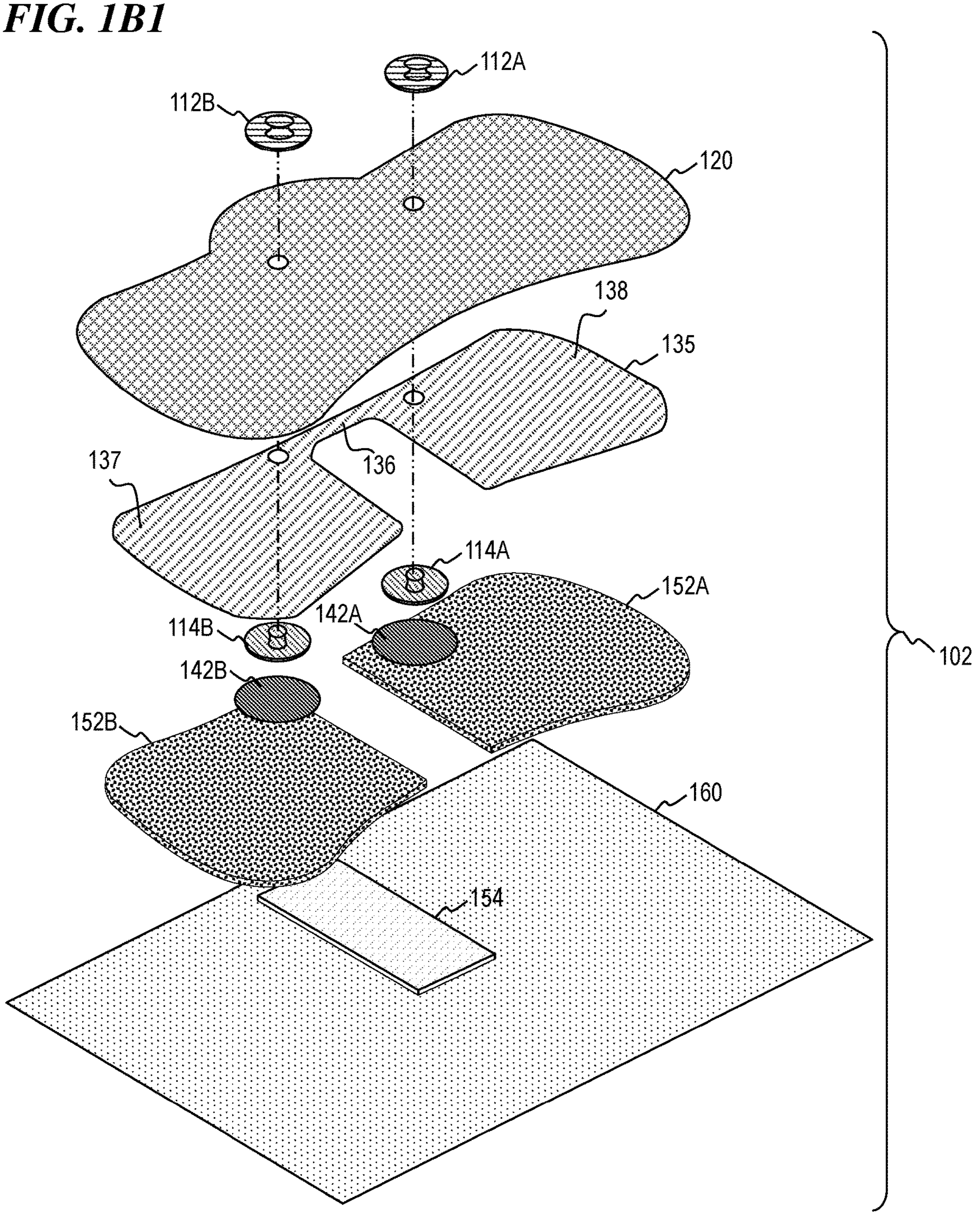

*FIG. 1B2*
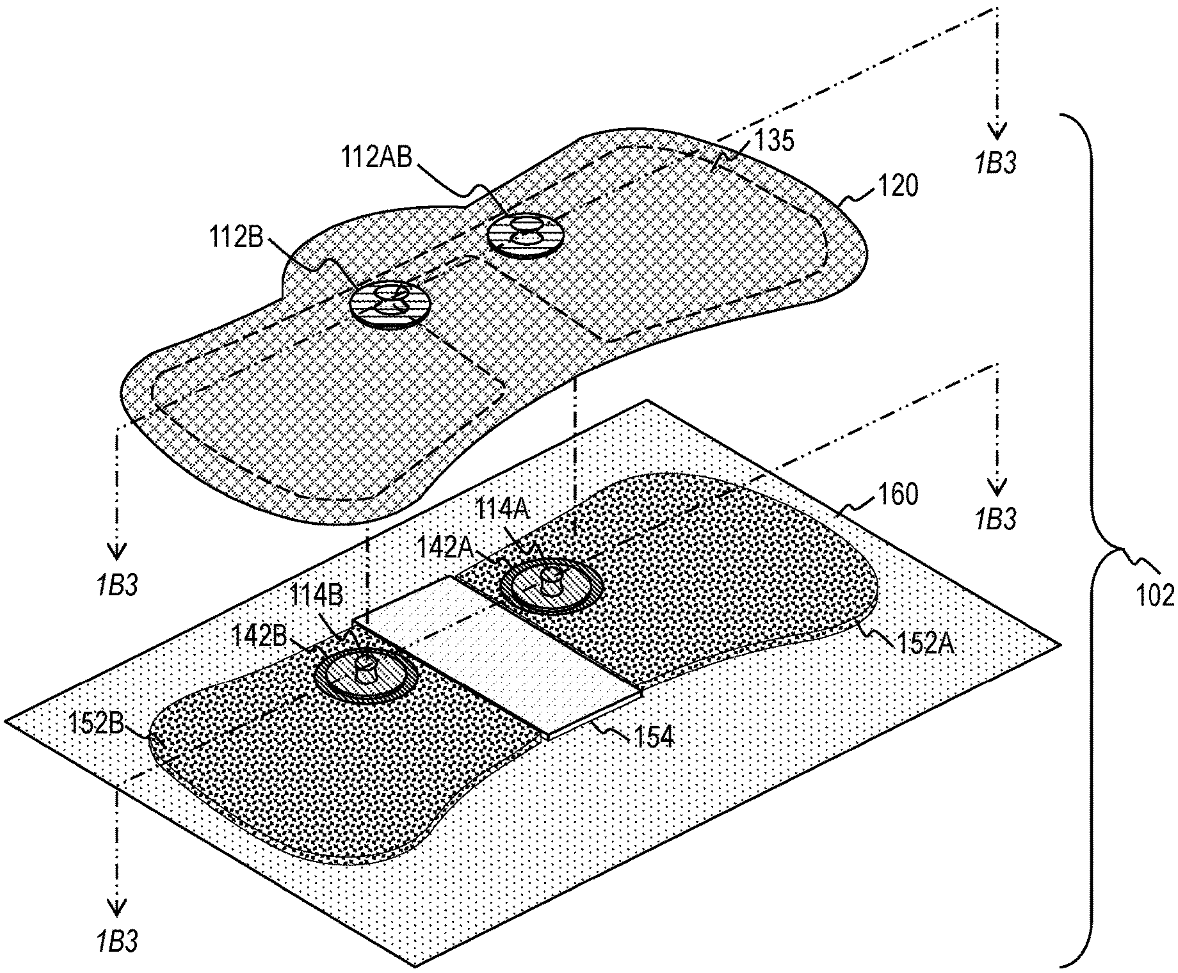
*FIG. 1B3*
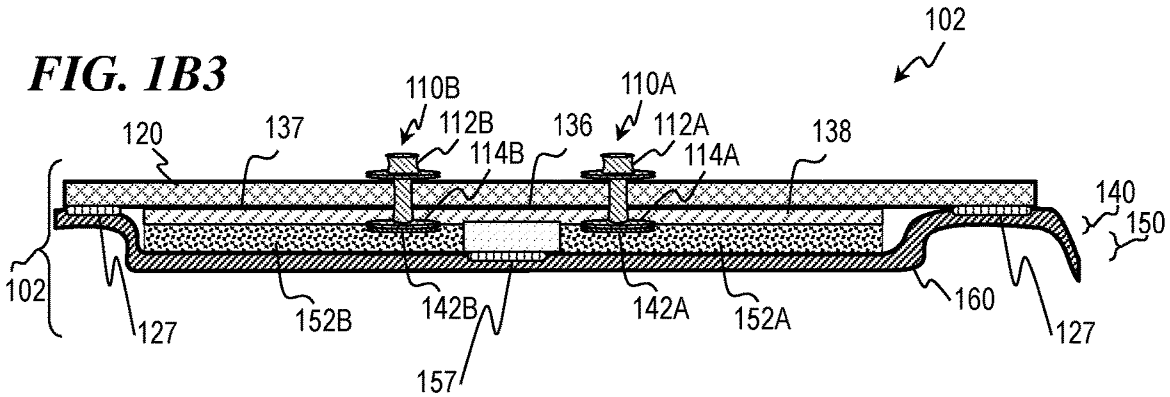

*FIG. 1C1*
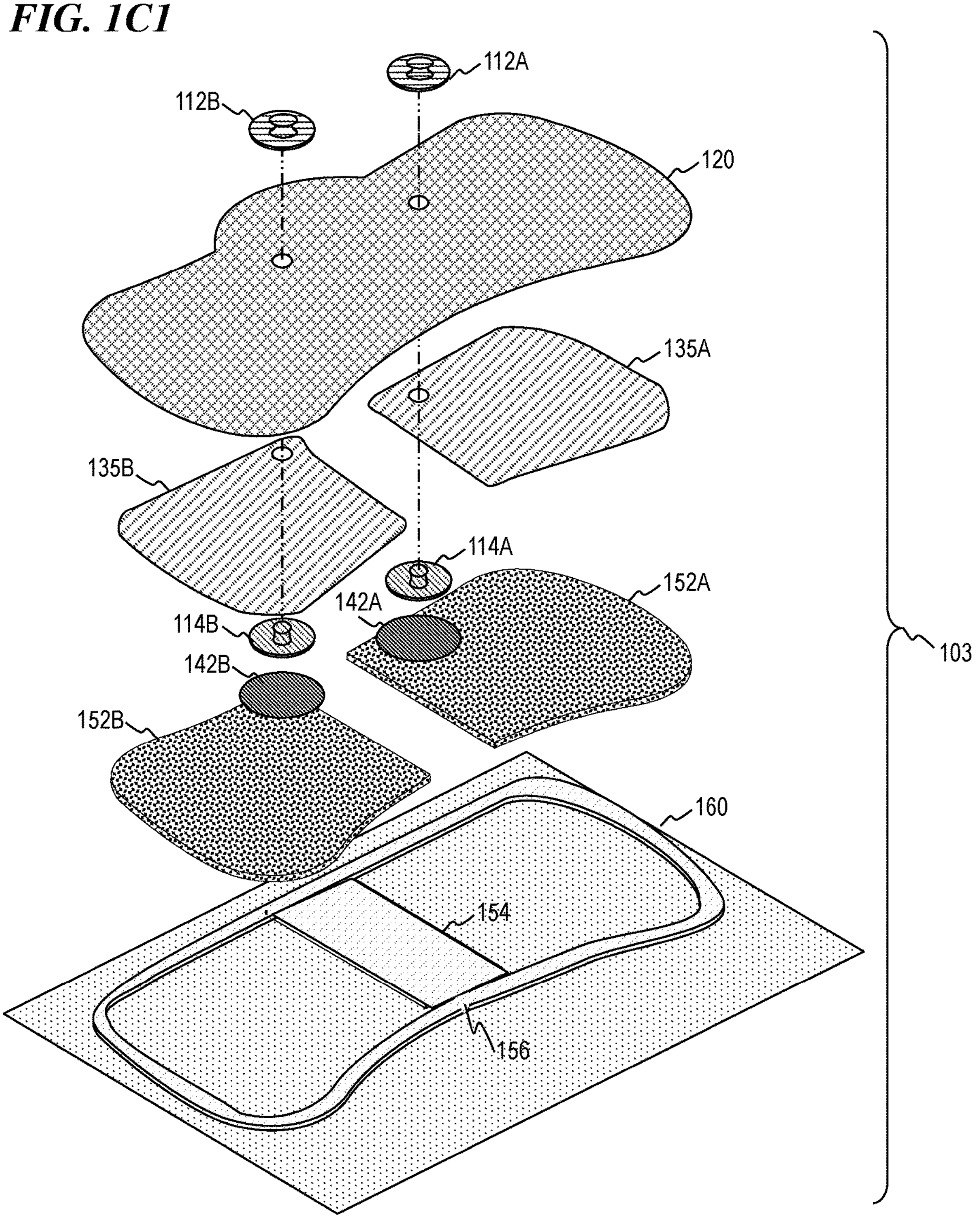

FIG. 1C2
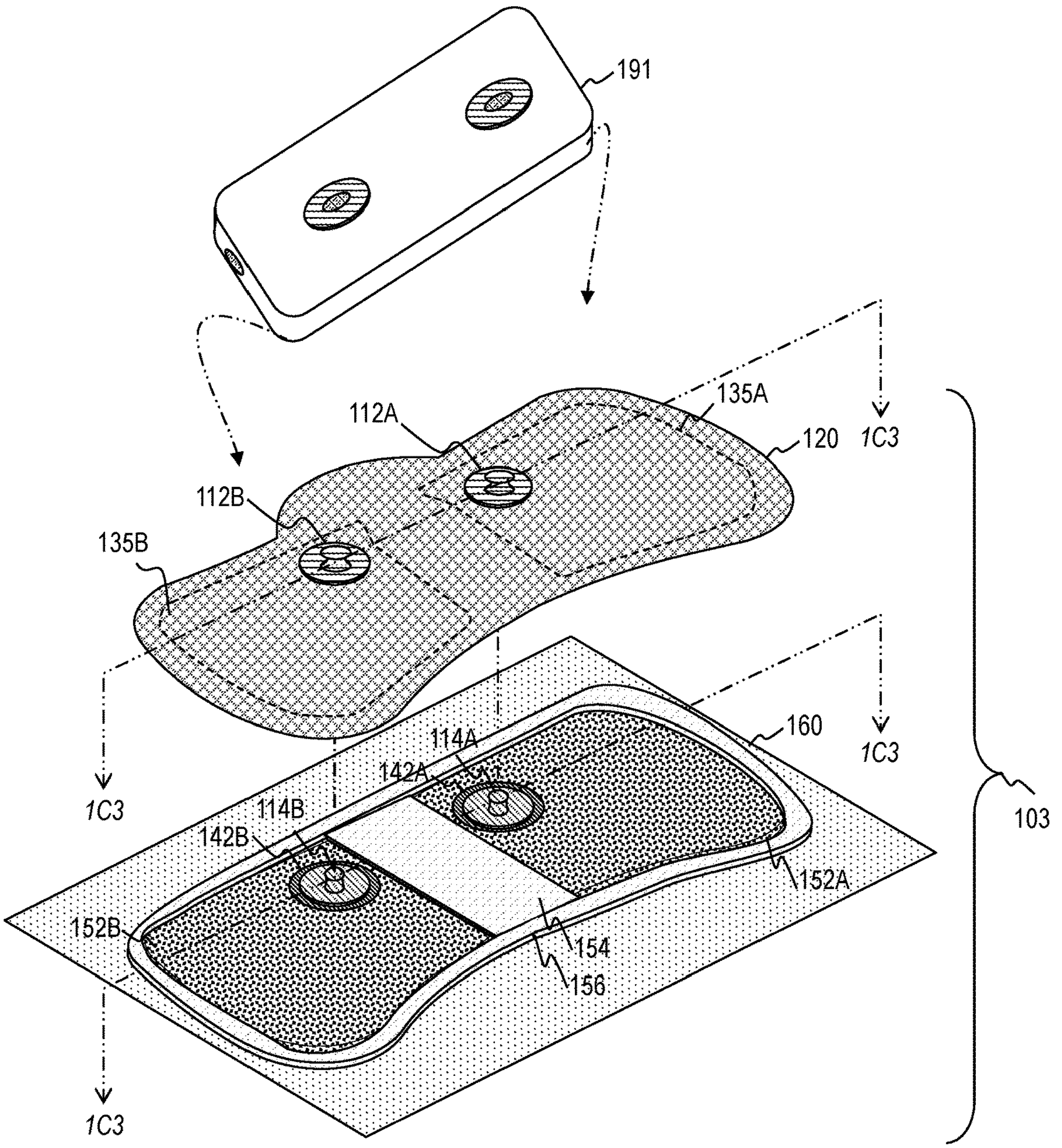
FIG. 1C3
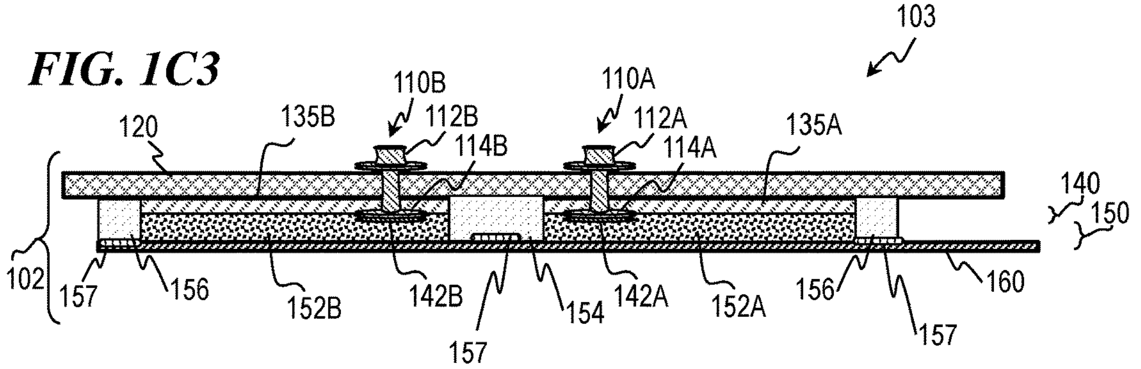

99
TABLET/PC CONTROLLER
98
WIRED/WIRELESS
203A
283
230
217
218
CONTRA-LATERAL RETURN ELECTRODE(S)
210
212
273
275
275
271
272

203B
284
217
230
218
CONTRA-LATERAL RETURN ELECTRODE(S)
210
212
272
273
275
271
275

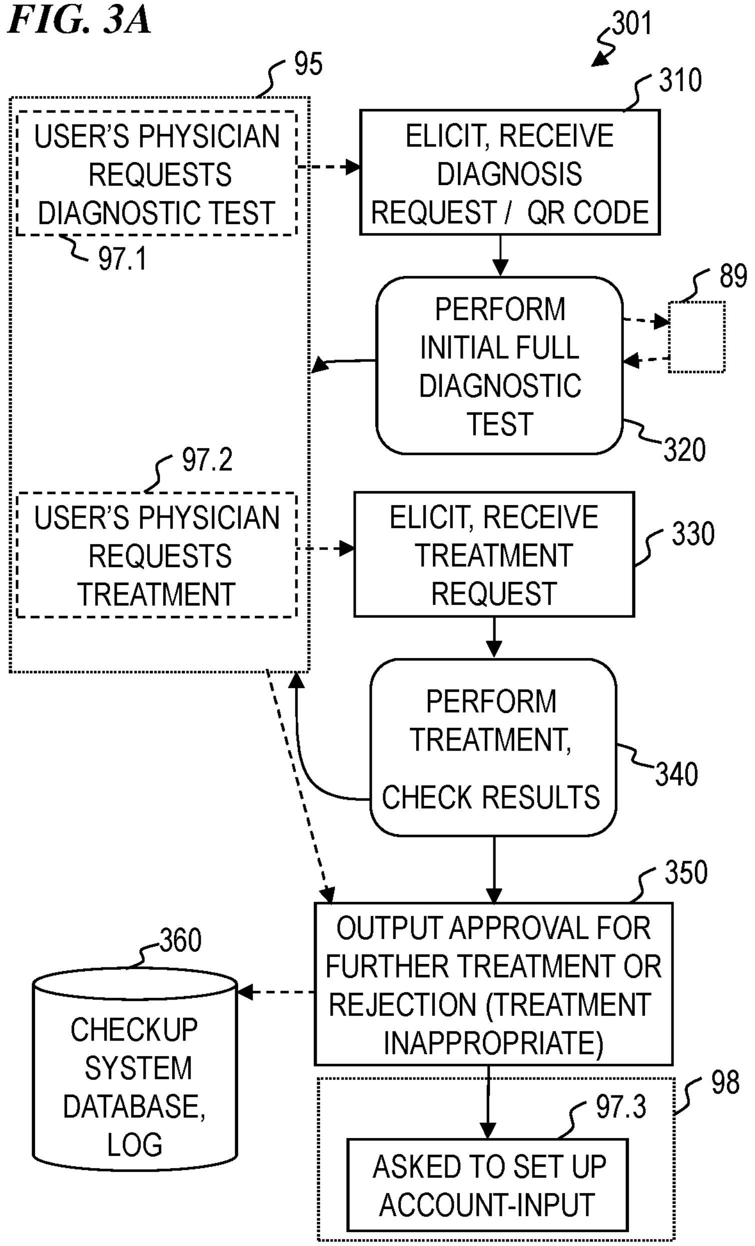

FIG. 3A
301
95
USER'S PHYSICIAN REQUESTS DIAGNOSTIC TEST
97.1
310
ELICIT, RECEIVE DIAGNOSIS REQUEST / QR CODE
PERFORM INITIAL FULL DIAGNOSTIC TEST
89
320
97.2
USER'S PHYSICIAN REQUESTS TREATMENT
ELICIT, RECEIVE TREATMENT REQUEST
330
PERFORM TREATMENT, CHECK RESULTS
340
350
OUTPUT APPROVAL FOR FURTHER TREATMENT OR REJECTION (TREATMENT INAPPROPRIATE)
360
CHECKUP SYSTEM DATABASE, LOG
98
97.3
ASKED TO SET UP ACCOUNT-INPUT

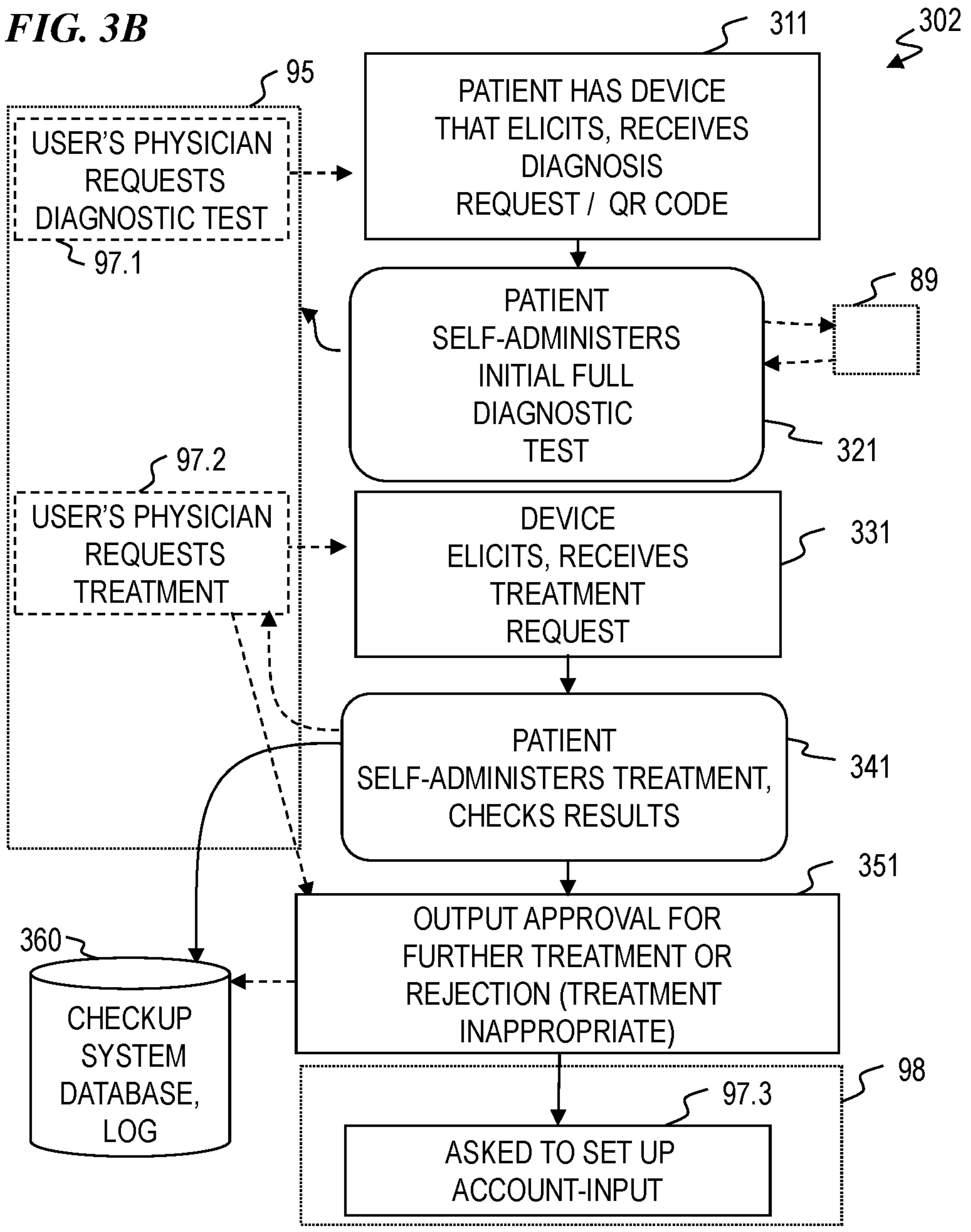

FIG. 3B
302
95
USER'S PHYSICIAN REQUESTS DIAGNOSTIC TEST
97.1
311
PATIENT HAS DEVICE THAT ELICITS, RECEIVES DIAGNOSIS REQUEST / QR CODE
89
PATIENT SELF-ADMINISTERS INITIAL FULL DIAGNOSTIC TEST
321
97.2
USER'S PHYSICIAN REQUESTS TREATMENT
DEVICE ELICITS, RECEIVES TREATMENT REQUEST
331
PATIENT SELF-ADMINISTERS TREATMENT, CHECKS RESULTS
341
351
360
OUTPUT APPROVAL FOR FURTHER TREATMENT OR REJECTION (TREATMENT INAPPROPRIATE)
CHECKUP SYSTEM DATABASE, LOG
98
97.3
ASKED TO SET UP ACCOUNT-INPUT 501
502
415
416
414
190
411
412
415
416
89

523
514
190
503
521
522

562
561
μP AND BATTERY
415
98
501
513
511
512
511
511
511
562
514
513
517
415

416
414
190
411
412
416
502

514
190
525
522
504

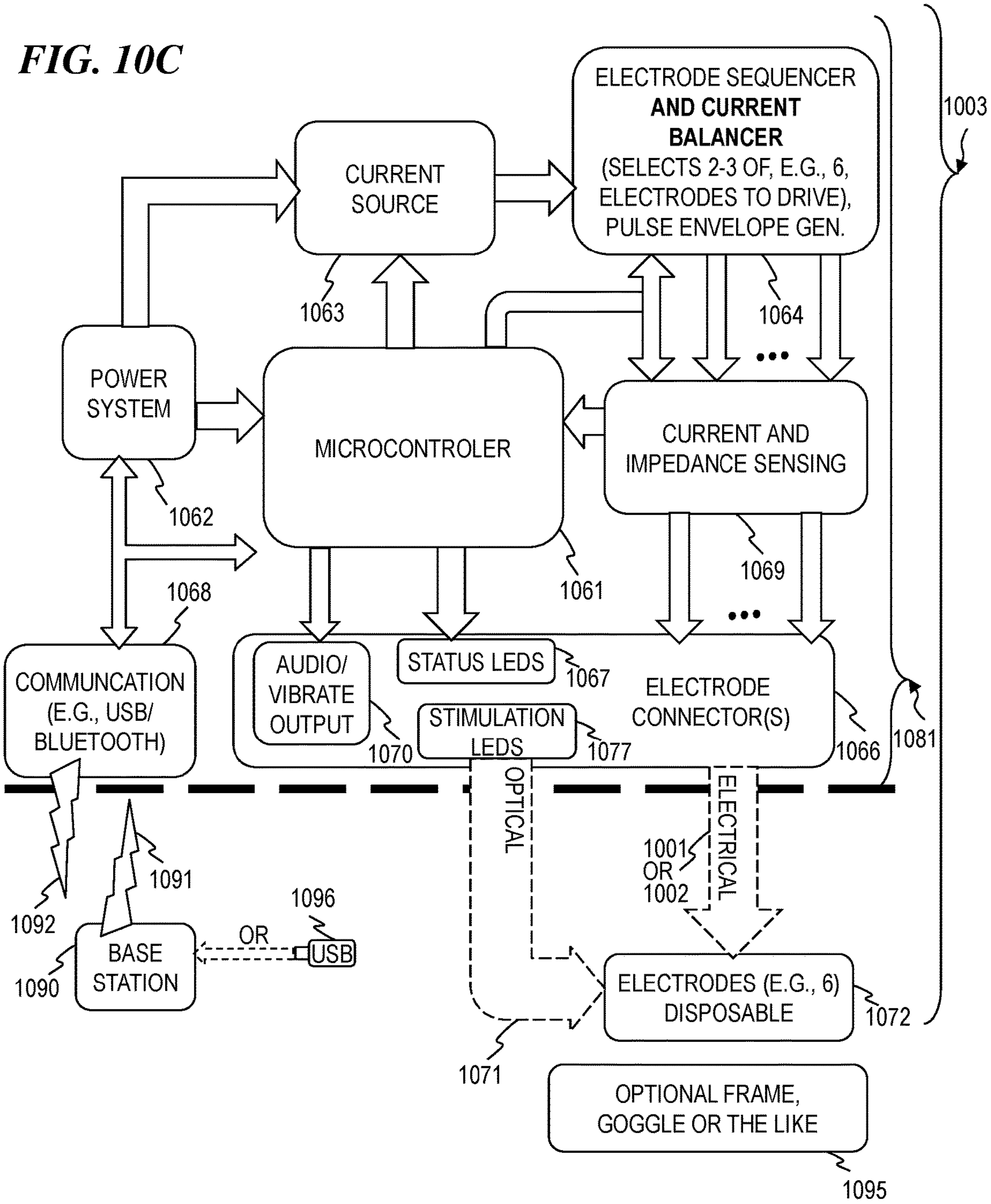

FIG. 10C
ELECTRODE SEQUENCER AND CURRENT BALANCER (SELECTS 2-3 OF, E.G., 6, ELECTRODES TO DRIVE), PULSE ENVELOPE GEN.
CURRENT SOURCE
1003
1063
1064
POWER SYSTEM
MICROCONTROLER
CURRENT AND IMPEDANCE SENSING
1062
1061
1069
1068
COMMUNCATION (E.G., USB/ BLUETOOTH)
AUDIO/ VIBRATE OUTPUT
STATUS LEDS
1067
ELECTRODE CONNECTOR(S)
STIMULATION LEDS
1070
1077
1066
1081
OPTICAL
ELECTRICAL
1001 OR 1002
1092
1091
1096
OR
USB
BASE STATION
1090
ELECTRODES (E.G., 6) DISPOSABLE
1072
1071
OPTIONAL FRAME, GOGGLE OR THE LIKE
1095

ELECTRODE SYSTEM FOR VISION TREATMENT AND METHOD

CROSS-REFERENCE TO RELATED APPLICATIONS

This application is a national-phase filing of, and claims priority benefit of, PCT Patent Application No. PCT/US2021/031869, filed May 11, 2021 by Thu-Ha Duncan, et al, and titled "Electrode system for vision treatment and method," which claims priority benefit, including under 35 U.S.C. § 119 (e), of U.S. Provisional Patent Application 63/025,987 filed May 15, 2020 by Thu-Ha Duncan, et al., titled "Electrode system for vision treatment and method," each of which is incorporated herein by reference in its entirety.

This application is related to:

U.S. Pat. No. 10,391,312 issued on Aug. 27, 2019 to Mowery et al. titled "Apparatus and method for ocular microcurrent stimulation therapy,"

PCT Patent Application No. PCT/US2016/051550, filed Sep. 13, 2016 by Mowery et al. titled "Apparatus and method for ocular microcurrent stimulation therapy" (published as WO 2017/048731), U.S. Provisional Patent Application No. 62/283,870, filed Sep. 15, 2015 by Mowery et al., titled "Appliance for microcurrent stimulation therapy using a disposable material afixed to the upper and lower eye lid & other body parts,"

U.S. Provisional Patent Application No. 62/283,871, filed Sep. 15, 2015 by Masko et al., titled "Apparatus for a method of application of microcurrent stimulation therapy, consisting of a goggle device affixed to & encircling the upper and/or lower eyelids, as well as other body parts,"

U.S. Provisional Patent Application No. 62/365,838, filed Jul. 22, 2016 by Tapp et al., titled "Appliance for micro-current stimulation,"

PCT Application Serial Number PCT/US2019/063404 filed on Nov. 26, 2019, by Masko et al., titled "APPARATUS AND METHOD FOR MICROCURRENT STIMULATION THERAPY" (published as WO 2020/131329), PCT Application Serial Number PCT/US2019/067627 filed on Dec. 19, 2019, by Masko et al., titled "MICRO-CURRENT-STIMULATION-THERAPY APPARATUS AND METHOD" (published as WO 2020/132337), U.S. Provisional Patent Application 62/783,116 filed on Dec. 20, 2018, by Masko et al., titled "APPARATUS AND METHOD FOR MICROCURRENT STIMULATION THERAPY," each of which is incorporated herein by reference in its entirety.

FIELD OF THE INVENTION

The present invention relates generally to electrical stimulation of the human body, and in particular, to systems and methods for electrode systems and signal delivery used in electrical-stimulation treatment, testing and monitoring of vision problems of a patient, analyzing the results of the treatments, and monitoring to determine, for example, whether a medical treatment for the patient needs to be continued and/or altered, wherein the design and placement of the electrode systems and adjustment of signals delivered to the electrodes facilitate adjustment of the geometry of signal flow through the tissues of the patient.

BACKGROUND OF THE INVENTION

U.S. Pat. No. 9,283,371 issued to Thu-Ha Duncan on Mar. 15, 2016 with the title "Electro-stimulation system" which is incorporated herein by reference. U.S. Pat. No. 9,283,371 describes an electro-stimulation system with a compact power and control assembly and a plurality of shaped gel electrode patches with instructions to facilitate user administration of therapy.

U.S. Pat. No. 8,888,288 issued to Iravani et al. on Nov. 18, 2014 with the title "Method and system for self-administering a visual examination using a mobile computing device," and is incorporated herein by reference in its entirety. U.S. Pat. No. 8,888,288 describes novel vision monitoring, screening, and testing tools and help-seeking enablers that may be used individually as or in combination with other vision monitoring and screening testing systems that improves patients' ability to recognize the onset and progression of visual changes over time. Patients' ability to identify acute or chronic visual conditions on their own may drive earlier help-seeking behavior by the patient, enable earlier clinical diagnosis by an eye care specialist, and therefore resulting in earlier treatment and reduced likelihood of severe vision loss.

U.S. Patent Application Publication 2008/0028214 by Tafoya et al. published on Jan. 31, 2008 with the title "Secure flash media for medical records" and is incorporated herein by reference in its entirety. Patent Application Publication 2008/0028214 describes a secure mobile device for storing data in a secure manner. The secure mobile device has a microarchitecture connected via an interface to flash memory on the device. The microarchitecture is able to authenticate the access of information stored on the secure mobile device using a private key. Upon authentication of the access of information, a record owner of the device may provide the stored information to third party trusted entities using an associated public key. The secure mobile device allows for secure transaction of confidential data on a variety of systems at a number of locations.

U.S. Patent Application Publication 2017/0188811 by Steven P. Lee published on Jul. 6, 2017 with the title "Comptuerized [sic] testing and determination of a visual field of a patient" and is incorporated herein by reference in its entirety. Patent Application Publication 2017/0188811 describes a system and method for testing and determining a visual field of a patient. In an example embodiment, a method includes instructing a computerized screen to display to a first visual field diagram to a patient, wherein the first visual field diagram includes a selected portion and instructing the patient to focus on the selected portion of the first visual field diagram. The example method also includes modifying the first visual field diagram to temporarily display an additional feature in an area corresponding to a part of the patient's visual field and receiving an input indicative that the patient saw the temporarily displayed additional feature. The example method further includes determining that the patient has vision in the part of the patient's visual field corresponding to the area in which the temporarily displayed additional feature was displayed based on the received input.

U.S. Pat. No. 9,237,842 issued to Lee, et al. on Jan. 19, 2016 with the title "Computerized refraction and astigmatism determination," and is incorporated herein by reference in its entirety. U.S. Pat. No. 9,237,842 describes generally a system and method for determining the refractive error of a patient, more particularly determining the patient's refractive error by using a computerized screen, and providing the patient with a prescription for the patient's preferred type of corrective lenses. The system and method do not require the trip or expense of a doctor visit, and are optimized for convenience and cost effectiveness. In a general embodiment, the present disclosure provides a method for determining a corrective lenses prescription of a patient. The method includes, separately, for each eye of the patient, determining the astigmatism prescription of the patient via a computerized screen, and determining the power of the corrective lenses' prescription of the patient via the computerized screen.

U.S. Patent Application Publication 2017/0290505 by Nico Correns, et al. published on Oct. 12, 2017 with the title "Visual field measuring device and system" and is incorporated herein by reference in its entirety. Patent Application Publication 2017/0290505 describes mobile computer devices, front-mounted optical systems and computer program products allowing perimetry measurement.

U.S. Patent Application Publication 2018/0049637 by Florencio Gonzalez Marquez, et al. published on Feb. 22, 2018 with the title "Open retinoscope couplable to a smartphone" and is incorporated herein by reference in its entirety. Patent Application Publication 2018/0049637 describes a novel open retinoscope comprising: a body (3) comprising a light source (31) oriented in the longitudinal direction and a first coupling means (32) for coupling to a Volk lens (51) holder in a longitudinally sliding manner; a Volk lens (51) holder (5), coupled in a longitudinally sliding manner to the body (3), where the holder (5) comprises a second longitudinal sliding coupling means (52) which is complementary to the first longitudinal sliding coupling means (32) of the body (3); and a smartphone adaptor (2) which can be connected to the body (3) in a transversely sliding manner.

U.S. Patent Application Publication 2018/0153399 by Wolfgang Fink, et al. published on Jun. 7, 2018 with the title "Smartphone-based handheld ophthalmic examination devices" and is incorporated herein by reference in its entirety. Patent Application Publication 2018/0153399 describes various examples of methods, systems and devices for ophthalmic examination. In one example, a handheld system includes an optical imaging assembly coupled to a user device that includes a camera aligned with optics of the optical imaging assembly. The user device can obtain ocular imaging data of at least a portion of an eye via the optics of the optical imaging assembly and provide ophthalmic evaluation results based at least in part upon the ocular imaging data. In another example, a method includes receiving ocular imaging data of at least a portion of an eye; analyzing the ocular imaging data to determine at least one ophthalmic characteristic of the eye; and determining a condition based at least in part upon the at least one ophthalmic characteristic.

U.S. Pat. No. 6,385,727 by Robert D. Cassagnol et al. issued on May 7, 2002 with the title "Apparatus for providing a secure processing" and is incorporated herein by reference in its entirety. U.S. Pat. No. 6,385,727 describes a secure processing environment. In one embodiment, the apparatus includes a read/write memory for storing encrypted information. It also includes a processor, a cipherer and an authenticator. The cipherer is in communication with the read/write memory for receiving encrypted information therefrom and is configured to decrypt the encrypted information into decrypted information to be returned to the memory for subsequent use by the processor. The authenticator authenticates the decrypted information prior to use by the processor and re-authenticates the information prior to re-encryption by the cipherer.

U.S. Pat. No. 9,839,352 by David A. Wallace et al. issued on Dec. 12, 2017 with the title "System, method and apparatus for enabling corneal topography mapping by smartphone" and is incorporated herein by reference in its entirety. U.S. Pat. No. 9,839,352 describes an apparatus for enabling corneal topography that includes an attachment to align a placido disc illumination system with a camera of a mobile communication device. The placido disc illumination system generates concentric rings and reflects the concentric rings off a cornea. A portion of the reflected concentric rings are utilized to confirm vertex distance. The apparatus further comprises a memory, a processor, and computer-readable instructions in a mobile communication device. The camera captures an image of reflected concentric rings and communicates the captured image of the reflected concentric rings to an external computing device. A method for performing corneal topography utilizes a mobile computing and/or communication device, projects a plurality of peripheral concentric rings onto a subject's cornea and projects center rings onto the subject's cornea. The method further includes capturing, via a smartphone camera, an image of the projected peripheral concentric rings and the center rings.

U.S. Pat. No. 6,736,511 by Plummer et al. issued May 18, 2004 with the title "Virtual reality peripheral vision scotoma screening" and is incorporated herein by reference in its entirety. U.S. Pat. No. 6,736,511 describes using a virtual reality display to present a random noise stimulus to a patient. Using an input device, a patient indicates the location of disturbances in the random noise display. In a preferred embodiment, a scanning retinal laser projects the random noise stimulus directly onto a patient's eye(s). The image is preferably presented at virtual infinity and can be imaged over the peripheral retina. A patient is directed to centrally fixate on the random noise display. A visual aid, such as a cross hair, may be included in the generated display to facilitate this focus. With a scanning laser virtual reality device having a narrow exit, the failure of a patient to centrally fixate causes the image presented to be distorted, incomplete or disappear from view. While a patient views the random noise display, the patient is directed to indicate any areas of disturbance using an input device. A preferred input device is a computer pen and tablet. This is easy to use while also viewing the random noise display. Preferably, the display changes when a patient uses the pen and tablet such that the patient sees the location being indicated either in place of or superimposed upon the random noise display.

U.S. Pat. No. 10,391,312 (listed above) describes devices and methods to deliver microcurrent stimulation therapy to the human body, when connected to a micro-stimulation current-generating apparatus. The method of applying microcurrent stimulation therapy to key points around the eye for treatment of problems such as macular degeneration, retinitis pigmentosa, glaucoma, optic neuritis and other eye-related or nerve-related conditions, as well as other diseases, such as Bell's Palsy, requiring localized stimulation to eyes and/or other body parts.

U.S. Pat. No. 6,035,236 issued to Jarding, et al. on Mar. 7, 2000 with the title "Methods and apparatus for electrical microcurrent stimulation therapy" and is incorporated herein by reference in its entirety. U.S. Pat. No. 6,035,236 describes an apparatus for supplying an electrical signal to a body part in order to provide microcurrent stimulation therapy to the body part. The apparatus preferably includes a first sweep wave or sweep frequency signal generator configured to generate a first sweep wave signal, a buffer amplifier circuit configured to receive the first sweep wave signal from the first sweep signal generator and amplify and buffer the sweep wave signal creating a buffered sweep wave signal. In addition, the apparatus preferably includes a current limiting circuit configured to receive the buffered sweep wave signal from the buffer amplifier circuit and limit the amount of current supplied to the body part. Finally, the apparatus preferably comprises a probe for applying the sweep wave signal to the body part. The apparatus may further comprise a second signal generator for generating a second signal which may comprise either a sweep wave signal or a non-sweep wave signal. The apparatus also will include a signal combining circuit configured to receive the first and second signals from the first and second signal generators and combine the first and second signals into a composite sweep wave signal.

U.S. Pat. No. 6,275,735 issued to Jarding et al. on Aug. 14, 2001 with the title "Methods and apparatus for electrical microcurrent stimulation therapy" and is incorporated herein by reference in its entirety. U.S. Pat. No. 6,275,735 describes a method and apparatus for providing microcurrent stimulation therapy to a body part. In one embodiment, a method allows digital control of the modulation frequency of the microcurrent signal. The method includes receiving a first digital data word which is used to produce a first frequency related to the first digital data word, whereupon, a first microcurrent signal at the first frequency is applied to the body part. A second digital data word is received and used to produce a second frequency related to the second digital data word. A second microcurrent signal at the second frequency is applied to the body part. In another embodiment, a method allows direct digital synthesis of the microcurrent stimulation signal. A first digital data word is used to produce a first analog voltage which is applied to the body part. A second digital data word is used to produce a second analog voltage which is also applied to the body part, where the first analog voltage is different from the second analog voltage. In yet another embodiment, an apparatus for providing microcurrent stimulation therapy includes a digital-to-analog converter, a controller and a plurality of data words. The controller is coupled to the digital-to-analog converter and supplies the digital-to-analog converter with digital data words in order to generate an electrical signal for the microcurrent stimulation therapy.

There is a need for an improved system and method for electrode design, placement, and electrical-stimulation-signal delivery and reception for vision-problem treatment and testing.

SUMMARY OF THE INVENTION

A system and method for electrode systems and signal delivery used in electrical-stimulation treatment, testing and monitoring of vision problems of a patient, analyzing the results of the treatments and monitoring to determine, for example, whether a medical treatment for the patient needs to be continued and/or altered, wherein the design and placement of the electrode systems, and the adjustment of signals delivered to various sets of electrodes facilitate adjustment of the geometry of signal flow through the tissues of the patient. In some embodiments, the treatment, testing and monitoring are for vision problems due to age-related macular degeneration (AMD).

BRIEF DESCRIPTION OF THE DRAWINGS

FIG. 1A1 is an exploded perspective-view diagram of a return-electrode system 101 for control of the geometry of electrical stimulation applied to human tissue, according to some embodiments of the present invention, for example, stimulation applied to the eyes when used in combination with eye electrodes.

FIG. 1A2 is a partially exploded perspective-view diagram of return-electrode system 101, according to some embodiments of the present invention.

FIG. 1A3 is a cross-section-view schematic diagram of return-electrode system 101, according to some embodiments of the present invention.

FIG. 1B1 is an exploded perspective-view diagram of a return-electrode system 102 for control of the geometry of electrical stimulation applied to human tissue, according to some embodiments of the present invention, for example, stimulation applied to the eyes when used in combination with eye electrodes.

FIG. 1B2 is a partially exploded perspective-view diagram of return-electrode system 102, according to some embodiments of the present invention.

FIG. 1B3 is a cross-section-view schematic diagram of return-electrode system 102, according to some embodiments of the present invention.

FIG. 1C1 is an exploded perspective-view diagram of a return-electrode system 103 for control of the geometry of electrical stimulation applied to human tissue, according to some embodiments of the present invention, for example, stimulation applied to the eyes when used in combination with eye electrodes.

FIG. 1C2 is a partially exploded perspective-view diagram of return-electrode system 103, according to some embodiments of the present invention.

FIG. 1C3 is a cross-section-view schematic diagram of return-electrode system 103, according to some embodiments of the present invention.

FIG. 3A is a block diagram/flow chart of an eye-stimulation system and method 301 for electrical stimulation applied to human eyes, according to some embodiments of the present invention.

FIG. 3B is a block diagram/flow chart of an eye-stimulation system and method 302 for electrical stimulation applied to human eyes, according to some embodiments of the present invention.

FIG. 10C is a block diagram of a system 1003 that can vary amplitude over time of signals as applied to an eye of a patient, such that the amplitude of the signals is both effective and not too uncomfortable to the patient, according to some embodiments of the present invention.

DESCRIPTION OF PREFERRED EMBODIMENTS

Figure 2A:
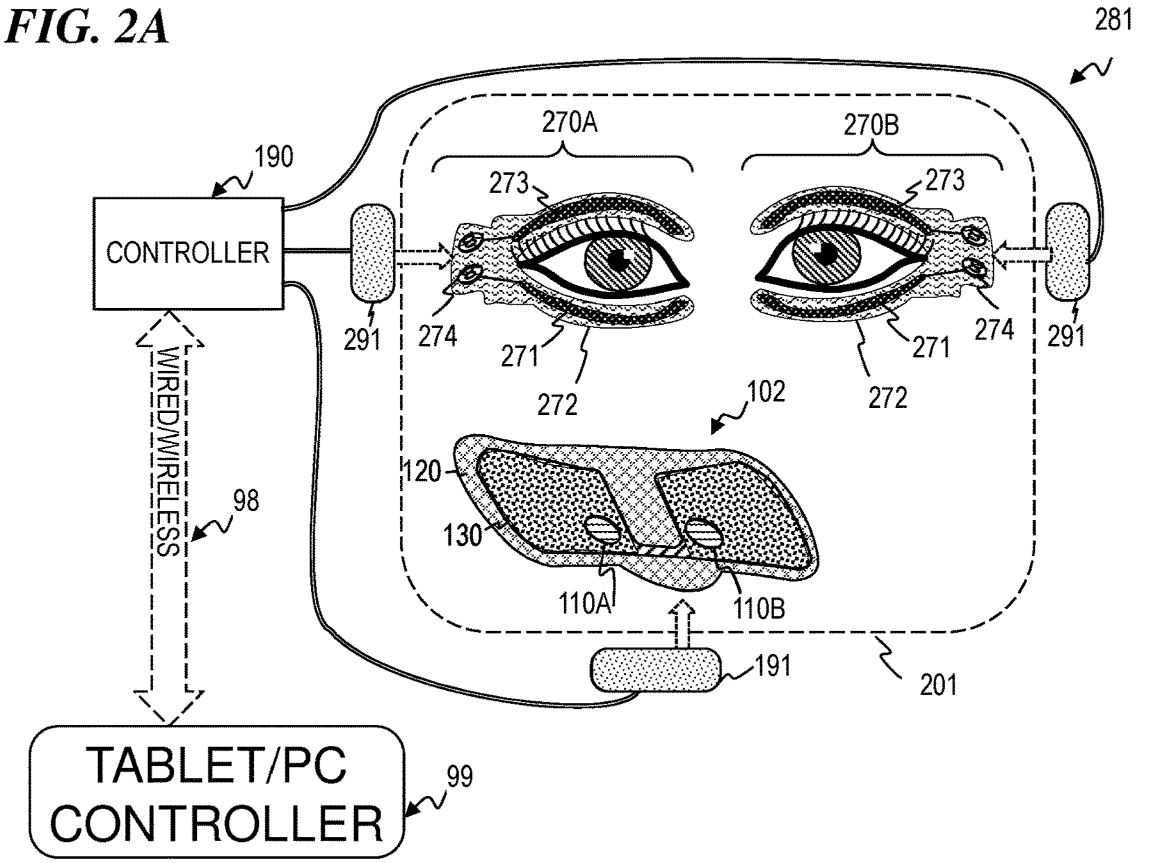
FIG. 2A is a perspective-view diagram of an eye-stimulation system 271 that uses an eye-stimulation electrode system 201 for control of the geometry of electrical stimulation applied to human eyes, according to some embodiments of the present invention.

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Certain marks referenced herein may be common-law or registered trademarks of third parties affiliated or unaffiliated with the applicant or the assignee. Use of these marks is for providing an enabling disclosure by way of example and shall not be construed to limit the scope of the claimed subject matter to material associated with such marks.

FIG. 1A1 is an exploded perspective-view diagram of a first type of return-electrode system 101 for control of the geometry of electrical stimulation applied to human tissue, according to some embodiments of the present invention, for example, stimulation applied to the eyes when used in combination with eye electrodes. In some embodiments, return-electrode system 101 includes two electrically conductive gel-layer areas 152A and 152B laterally offset from one another and, in some embodiments, separated by an insulator 154 positioned edge-to-edge between gel-layer areas 152A and 152B. In some embodiments, insulator 154 includes a pressure-sensitive adhesive. In some embodiments, insulator 154 not only separates gel-layer areas 152A and 152B but also surrounds the perimeters of gel-layer areas 152A and 152B. In some embodiments, positioned face-to-face and in electrical conduction with gel-layer areas 152A and 152B is a single electrically conductive metallic electrode 130 having one or more openings through which one or more snap-type electrical connections 110 are assembled. In the embodiment shown, two snap-type electrical connections 110 are provided, including their respective inner portions 114A and 114B, and their respective outer portions 112A and 112B. Other embodiments include one or more such snap-type connectors 110 or other suitable electrical connectors. In some embodiments, the one or more snap-type electrical connections 110 are configured to be connected to a self-contained electrical-simulation controller that is also electrically connected (e.g., via one or more cables or flex circuitry) to electrodes above and below one or both eyes of a patient. In some embodiments, the respective inner snap-assembly portions 114A and 114B are separated from their respective gel-layer areas 152A and 152B by respective carbon-layer disks 142A and 142B. In some embodiments, electrically conductive metallic electrode 130 is deposited on insulating polymer substrate 120. In some embodiments, substrate 120 has a pressure-sensitive adhesive around its perimeter, and a removable release layer 160 is provided, such that the assembled return-electrode system 101 can be used by removing release layer 160 and applying return-electrode system 101 to the desired area of the patient's skin (in some embodiments, return-electrode system 101 is applied to the patient's skin at the back of the patient's head as shown, for example, in FIGS. 6A-9B, while, in other embodiments, return-electrode system 101 is applied to the patient's skin in any other suitable location (e.g., the patient's neck, temple, shoulder, palm, or the like)), with the perimeter of pressure-sensitive adhesive holding it in place and containing the gel-layer areas 152A and 152B in place and separated from one another. In some embodiments, the two larger side areas 132 and 133 of electrode 130 are electrically connect to one another via bridge area 131.

In some embodiments, two larger side areas 132 and 133 of electrode 130 and the gel-layer areas 152A and 152B are made bilaterally symmetric and as similar to one another as possible in order that equal or substantially equal amounts of current flow through the patient's tissue between the eye electrode(s) and each of the two halves of electrode 130 and their gel-layer areas 152A and 152B.

In some embodiments, return-electrode system 101 can be considered as either grounding or as an active electrode relative to the electrodes placed on the patient's eyes. This allows for two laterally separated active zones at the back of the patient's head driven simultaneously with one electrical input (or channel). Some other embodiments of the present invention achieve this with splitting lead wires, this embodiment achieves this result with a single electrode having two physically separated contact areas (each one optionally using an electrically conductive gel for better conductivity and more equal electrical conductivity to the patient's skin). In some embodiments, this allows controlling the electric field to better reach the central areas of the nerves connecting the eyes to the optical portions of the brain.

Although there are two snaps shown in the embodiments of FIGS. 1A1-1A3, other embodiments use only one snap electrical connection. In other embodiments, other numbers or other types of electrical connectors are provided.

The embodiment shown in FIGS. 1A1-1A3, is designed to equally distribute the electricity for symmetrical current density across the back of the head, but other embodiments are designed to have unequal-sized side areas 132 and 133 or to have other parameters to achieve asymmetrical current density based on a desired effect.

In various embodiments, different sizes are provided, and are selected based on ongoing diagnostic results of a particular patient's treatment progress or the progress of a population of patients who are enrolled in a controlled experiment to determine an optimal size for a given physiology.

Some embodiments use a conductive hydrogel. In other embodiments, other suitable conductive medium(s) are used.

The multiple connection points allows for more than one channel (e.g., in some embodiments, differential outputs from the different operational amplifiers used for the right eye electrode(s) versus the left-eye electrodes) to share return-electrode system 101 for the purposes of signal return or grounding.

FIG. 1A2 is a partially exploded perspective-view diagram of return-electrode system 101, according to some embodiments of the present invention. FIG. 1A2 shows the components that are separated in FIG. 1A1 as partially assembled, according to some embodiments of the present invention.

FIG. 1A3 is a cross-section-view schematic diagram of the assembled return-electrode system 101, according to some embodiments of the present invention, with the vertical proportions exaggerated for illustrative purposes. Note that in this embodiment, the electrically conductive hydrogel areas 152A and 152B extend beyond the lateral boundaries of conductor 130's left and right-hand areas 132 and 133 to allow easier alignment, but most of the current will flow vertically since that is the shortest path with the least resistance. In some embodiments, the top substrate 120 includes a pressure-sensitive adhesive 127 around its perimeter adjacent the release layer 160. Release layer 160 and/or substrate 120 are flexible enough to seal to one another to enclose the gel areas 152A and 152B before the release layer 160 is removed when the product is about to be applied to the skin of the patient. In some embodiments, the central insulator 154 also is coated on its skin-facing surface with pressure-sensitive adhesive 157.

FIG. 1B1 is an exploded perspective-view diagram of a return-electrode system 102 for control of the geometry of electrical stimulation applied to human tissue, according to some embodiments of the present invention, for example, stimulation applied to the eyes when used in combination with eye electrodes. In some embodiments, return-electrode system 102 is substantially similar to return-electrode system 101 of FIGS. 1A1-1A3, except that the electrode 135 has side-conductor areas 137 and 138 that extend to the entire areas within the respective perimeters of gel areas 152A and 152B, allowing the entire electrically conductive gel surface areas of 152A and 152B to be in contact with electrode 135 for more equal and constant voltage and/or current for the entire skin areas contacted. In some embodiments, a central bridge conductor 136 electrically connects side-conductor areas 137 and 138 to one another. In some embodiments (not shown here, but in a manner similar to that shown in FIGS. 1C1-1C3) a perimeter ring of insulator material having pressure-sensitive contact adhesive 157 is provided surrounding the gel areas 152A and 152B.

FIG. 1B2 is a partially exploded perspective-view diagram of return-electrode system 102, according to some embodiments of the present invention. FIG. 1B2 shows the components that are separated in FIG. 1B1 as partially assembled, according to some embodiments of the present invention.

FIG. 1B3 is a cross-section-view schematic diagram of return-electrode system 102, according to some embodiments of the present invention. Note that the side-conductor areas 137 and 138 that extend to the entire areas within the respective perimeters of gel areas 152A and 152B.

FIG. 1C1 is an exploded perspective-view diagram of a return-electrode system 103 for control of the geometry of electrical stimulation applied to human tissue, according to some embodiments of the present invention, for example, stimulation applied to the eyes when used in combination with eye electrodes. In some embodiments, return-electrode system differs from return-electrode system 101 of FIGS. 1A1-1A3, in that two respective electrodes 135A and 135B are electrically separated and independently driven and each extends to the entire respective areas within the respective perimeters of gel areas 152A and 152B, allowing the entire respective gel surface areas of 152A and 152B to be in contact with respective electrodes 135A and 135B so that the separate control of the signals provided to each of respective electrodes 135A and 135B can achieve either more equal and constant voltage and/or current for the skin areas contacted, or alternatively, the signals can be controlled to have different unequal currents and/or voltages in order to shape the electric field across the tissues (e.g., of the eyes, optical nerves, and/or brain) between the eye(s) being stimulated and the return electrode system 103. See FIGS. 6A-9B. In some embodiments as shown here, a perimeter ring 156 of insulator material having pressure-sensitive contact adhesive 157 is provided surrounding (and thus containing) the gel areas 152A and 152B.

FIG. 1C2 is a partially exploded perspective-view diagram of return-electrode system 103, according to some embodiments of the present invention. FIG. 1C2 shows the components that are separated in FIG. 1C1 as partially assembled, according to some embodiments of the present invention.

FIG. 1C3 is a cross-section-view schematic diagram of return-electrode system 103, according to some embodiments of the present invention.

FIG. 2A is a perspective-view diagram of an eye-stimulation system 281 that uses an eye-stimulation electrode system 201 for control of the geometry of electrical stimulation applied to human eyes, according to some embodiments of the present invention. In some embodiments, eye-stimulation electrode system 201 includes return-electrode system 102 (as described above for FIGS. 1B1, 1B2, and 1B3) and two eye-electrode systems 270A and 270B for the patient's left and right eyes, respectively. Electrical connector 191 provides electrical connectivity between controller 190 and return-electrode system 102, while electrical connectors 291 each respectively provides electrical connectivity between controller 190 and eye-electrode systems 270A and 270B. In other embodiments, return-electrode system 101 (as described above for FIGS. 1A1, 1A2, and 1A3) or return-electrode system 103 (as described above for FIGS. 1C1, 1C2, and 1C3) are substituted for return-electrode system 102. In some embodiments, controller 190 supplies pulsed signals to connector 191 and the two connectors 291 that provide electrical stimulation through the upper and lower eyelids of the patient to provide therapeutic stimulation designed to counteract age-related macular degeneration (AMD). In some embodiments, the polarity of the signals are periodically reversed to reduce charge buildup in the tissues of the patient. In some embodiments, the magnitude of the signals when reversed is changed (e.g., longer duration or more numerous pulses at a lower magnitude of electrical current being used to neutralize charge buildup of shorter duration or less numerous pulses at a higher magnitude of electrical current). In some embodiments, a pulse envelope is applied to amplitude modulate a carrier of higher-frequency shorter pulses. In some embodiments, the pulse envelope is gradually ramped to higher magnitude intensity so as to avoid unpleasant sensory nerve stimulation (See FIGS. 10A, 10B, and 10C and their description below). In some embodiments, each eye-electrode subsystem 270A, 270B includes a lower-eye-lid electrode 272 and a upper-eye-lid electrode 273 deposited as metal layers on a flexible insulating substrate 271, each electrode having a respective snap-type electrical connector 274 (or other suitable connector). Connectors 291 each have a corresponding receiver connector for each connector 274.

In some embodiments, using three separate parts, as is the case of eye-stimulation electrode system 201, allows easier application of the parts since they can be applied one at a time and accommodate easily to different head sizes. In some embodiments, each of the three parts has an individual QR-type code (with encoded serial number information-see, e.g., FIG. 2G and its description) printed thereon (or, in other embodiments (not shown), a chip having such encoded serial number information), so that a camera app (or other suitable software app) on a smartphone or tablet 99 can read the respective QR codes to track which electrodes were used on which patient at what date and time for such purposes as tracking therapy (so adjustments can be made at future therapy sessions) and/or patient/insurance billing or the like.

Figure 2B:
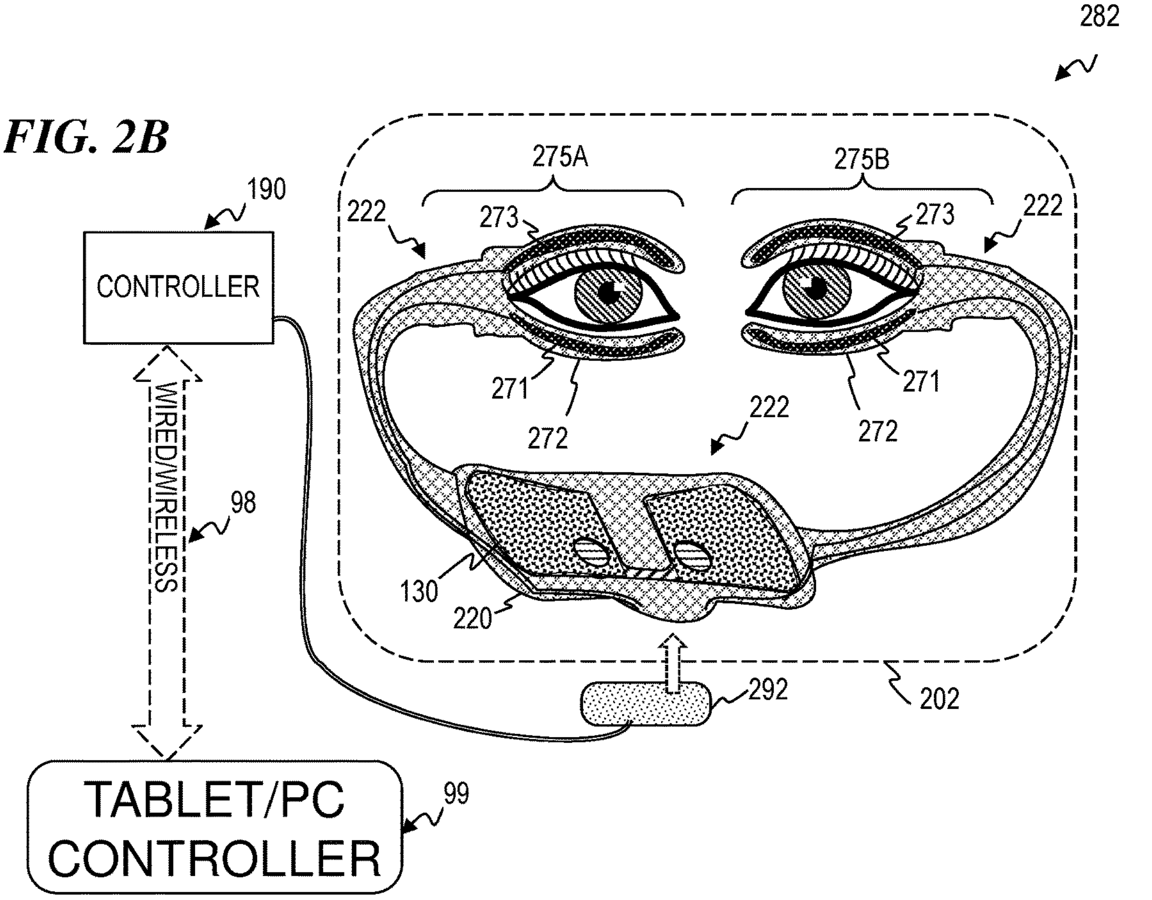
FIG. 2B is a perspective-view diagram of an eye-stimulation system 272 that uses an eye-stimulation electrode system 202 for control of the geometry of electrical stimulation applied to human eyes, according to some embodiments of the present invention.

FIG. 2B is a perspective-view diagram of an eye-stimulation system 282 that uses an eye-stimulation electrode system 202 for control of the geometry of electrical stimulation applied to human eyes, according to some embodiments of the present invention. In some embodiments, eye-stimulation system 282 is operated in a manner substantially similar to the operation of eye-stimulation system 281 described above, except that eye-stimulation electrode system 202 is fabricated as an all-in-one electrode system rather than three separate parts, as in the case of eye-stimulation electrode system 201. In some embodiments, a single electrical connector 292 has suitable connection points to couple signals to all of the respective electrodes (e.g., 130, 271, 273).

Figure 2C:
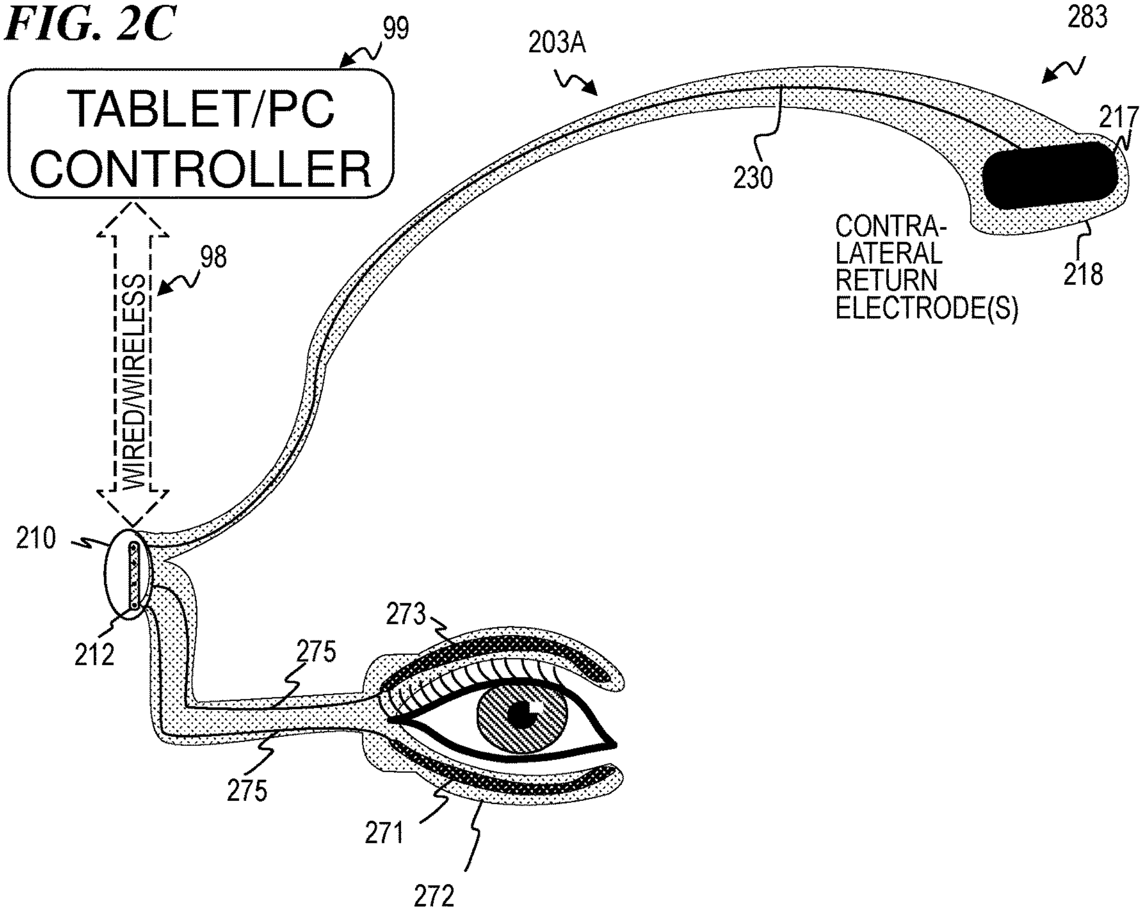
FIG. 2C is a perspective-view diagram of an eye-stimulation system 273 that uses an eye-stimulation electrode system 203 for control of the geometry of electrical stimulation applied to a human eye, according to some embodiments of the present invention.

FIG. 2C is a perspective-view diagram of an eye-stimulation system 283 that uses an eye-stimulation electrode system 203A for control of the geometry of electrical stimulation applied to human eyes, according to some embodiments of the present invention. In some embodiments, interfacing the system to 190 is the connector 210 with individual connection points 212. The contralateral return electrodes interface electrode 217 on substrate 218 though electrical connecting wire pathway 230. In some embodiments, eye-stimulation electrode system 203A provides a pair of electrodes 271 and 273 for the patient's left eye and a contralateral electrode for the right back side of the patient's head (essentially similar to one-third of system 206 of FIG. 2F).

Figure 2D:
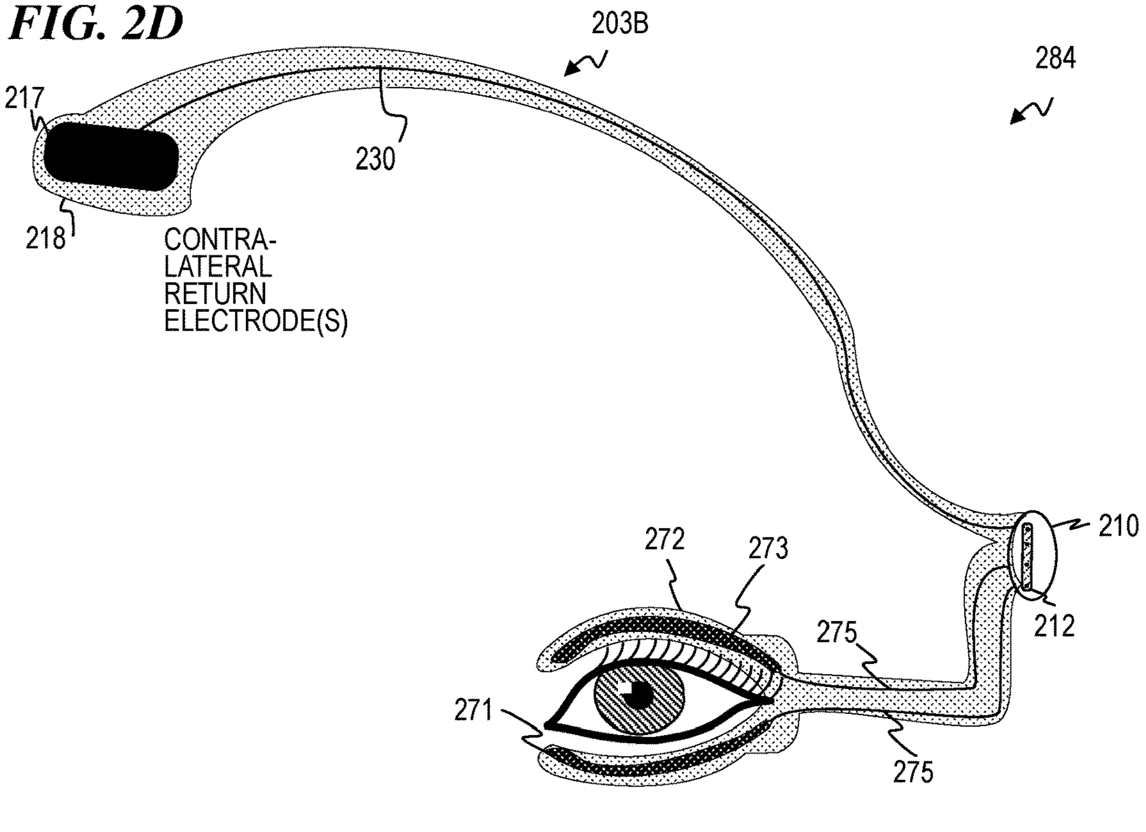
FIG. 2D is a perspective-view diagram of an eye-stimulation system 274 that uses an eye-stimulation electrode system 204 for control of the geometry of electrical stimulation applied to a human eye, according to some embodiments of the present invention.

FIG. 2D is a perspective-view diagram of an eye-stimulation system 284 that uses an eye-stimulation electrode system 203B for control of the geometry of electrical stimulation applied to a human eye, according to some embodiments of the present invention. In some embodiments, interfacing the system to 190 is the connector 210 with individual connection points 212. The contralateral return electrodes interface electrode 217 on substrate 218 though connecting wire pathway 230. In some embodiments, eye-stimulation electrode system 203A provides a pair of electrodes 271 and 273 for the patient's right eye and a contralateral electrode for the left back side of the patient's head (essentially similar to one-third of system 206 of FIG. 2F).

Figure 2E:
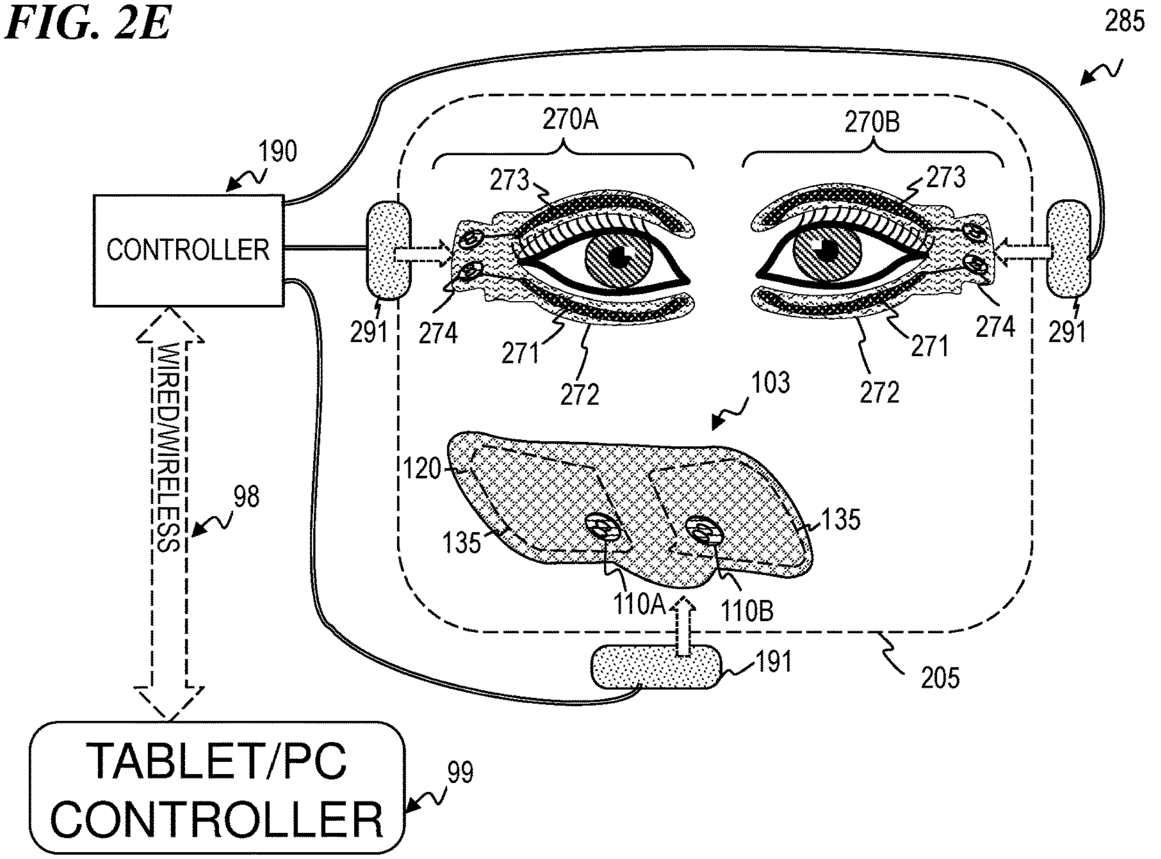
FIG. 2E is a perspective-view block diagram of an eye-stimulation system 275 that uses an eye-stimulation electrode system 205 for control of the geometry of electrical stimulation applied to a human eye, according to some embodiments of the present invention.

FIG. 2E is a perspective-view block diagram of an eye-stimulation system 285 that uses an eye-stimulation electrode system 205 for control of the geometry of electrical stimulation applied to a human eye, according to some embodiments of the present invention. In some embodiments, eye-stimulation electrode system 205 is similar to eye-stimulation electrode system 201, except that the return electrodes 135 are electrically separate and individually activatable.

Figure 2F:
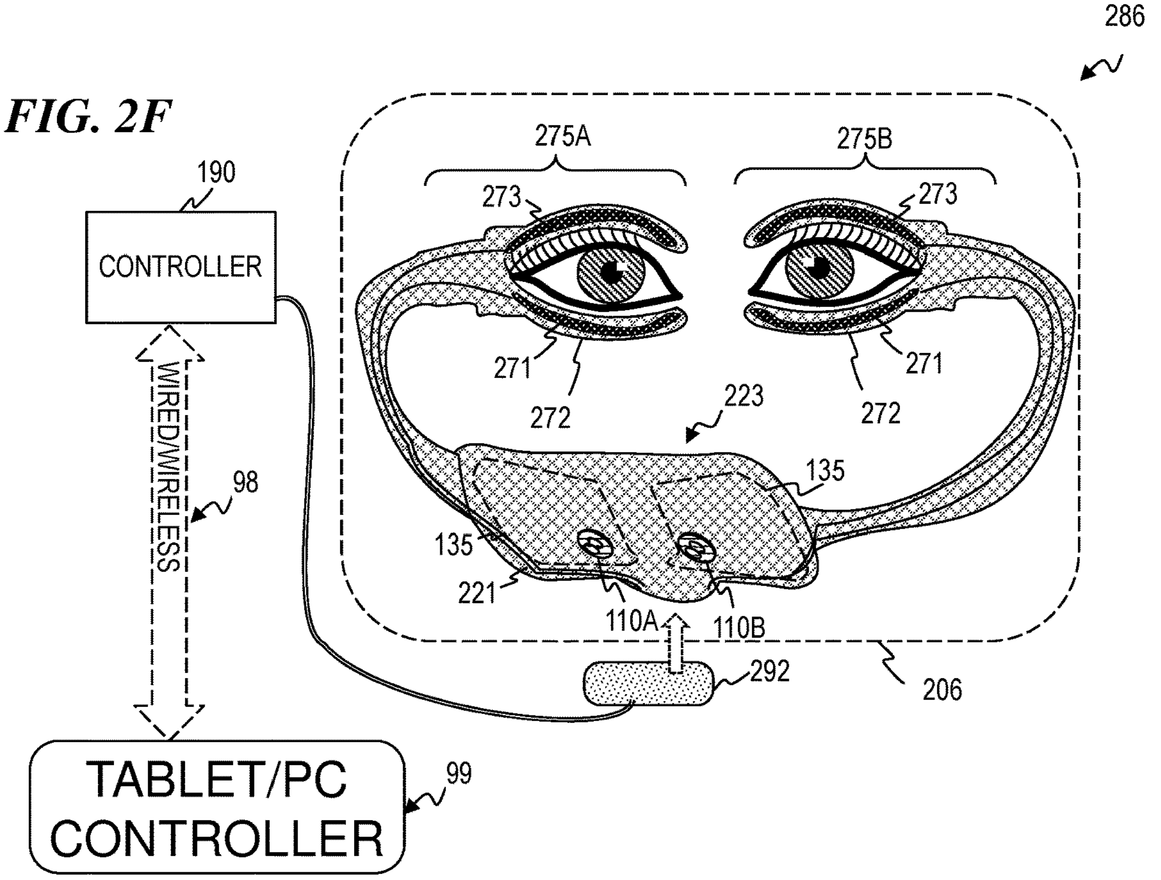
FIG. 2F is a perspective-view block diagram of an eye-stimulation system 276 that uses an eye-stimulation electrode system 206 for control of the geometry of electrical stimulation applied to a human eye, according to some embodiments of the present invention.

FIG. 2F is a perspective-view block diagram of an eye-stimulation system 286 that uses an eye-stimulation electrode system 206 for control of the geometry of electrical stimulation applied to a human eye, according to some embodiments of the present invention. In some embodiments, eye-stimulation electrode system 206 is similar to eye-stimulation electrode system 202, except that the return electrodes 135 are electrically separate and individually activatable.

Figure 2G:
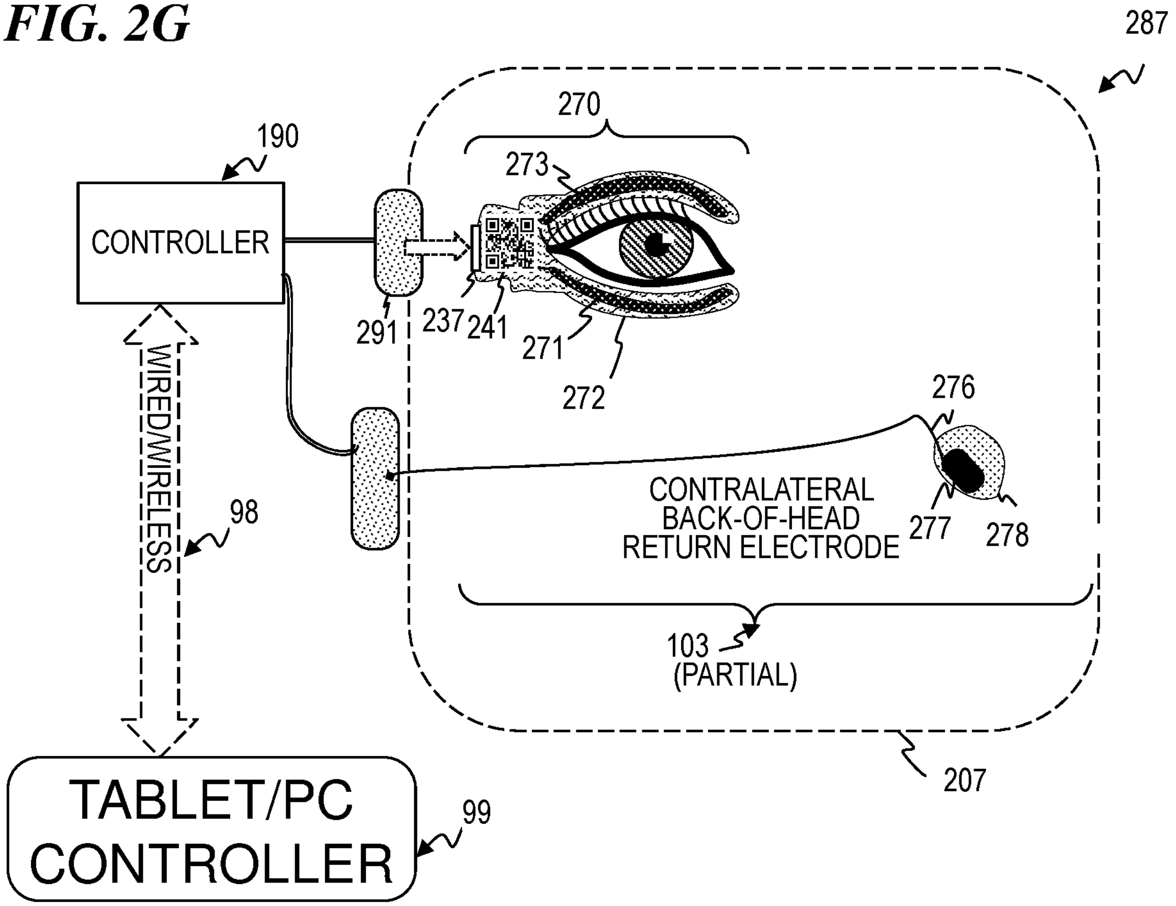
FIG. 2G is a perspective-view block diagram of an eye-stimulation system 287 that uses an eye-stimulation electrode system 207 for control of the geometry of electrical stimulation applied to a human eye, according to some embodiments of the present invention.

FIG. 2G is a perspective-view block diagram of an eye-stimulation system 287 that uses an eye-stimulation electrode system 207 for control of the geometry of electrical stimulation applied to a human eye, according to some embodiments of the present invention. In some embodiments, eye-stimulation electrode system 206 is similar to eye-stimulation electrode system 202, except that the return electrode 117 is both physically and electrically separate and individually attachable to the patient and individually activatable. In some embodiments, a DR-type code 241 (having an encoded serial number and/or information usable to look up the serial number on the internet via an app on a smartphone or tablet 99) is attached to electrode system 270.

FIG. 3A is a block diagram/flow chart of an eye-stimulation system and method 301 for electrical stimulation applied to human eyes, according to some embodiments of the present invention. In some embodiments, method 301 includes block 97.1 representing a physician 95 taking an action, wherein the physician 95 is attending to a patient/user 89. In some embodiments, action 97.1 requests/schedules a diagnostic test from a facility suited for such testing. In some embodiments, the request includes a scan of the Quick Response (QR) code located on the eye-stimulation electrode system being used for patient 89 (in some such embodiments, the QR code includes the serial number associated with the eye-stimulation electrode system being used). In some embodiments, at block 310, the testing facility elicits and receives the test request and/or the scanned QR-code information. In some embodiments, at block 320, the diagnostic test is administered at the testing facility, a data report of the diagnostic test is generated, and the data report is delivered to the patient's/user's physician 95, who, based on the report, at block 97.2 requests a treatment (a treatment that is performed at the testing facility as shown by block 340, such as, for example, those treatments described in U.S. Pat. Nos. 10,391,312, 6,035,236, and/or 6,275,735 set forth above). In some embodiments, at block 330, the testing facility elicits and receives the treatment request from the physician 95. In some embodiments, block 340 also includes performing a follow-on diagnostic test, such as done at block 320, to see if there are any immediate improved results. In some embodiments, at block 350, the results from the follow-on diagnostic test performed as part of block 340 are checked (in some embodiments, optionally including a review by physician 95), and if appropriate, an approval or rejection (as appropriate) is issued at block 350, and provided to the user/patient 89 and stored in database 360 that maintains a log of patients and results of checkups. In some embodiments, at block 97.3, a person 98 (e.g., the user/patient 89 and/or the user's/patient's physician 95) sets up an account in the database 360 for a series of ongoing treatments over a period of time.

FIG. 3B is a block diagram/flow chart of an eye-stimulation system and method 302 for electrical stimulation applied to human eyes, according to some embodiments of the present invention. In some embodiments, action 97.1 requests/schedules a diagnostic test, but instead of the diagnostic test and/or treatment being performed at a facility suited for such testing as in FIG. 3A, patient 89 has the eye-stimulation electrode system in their possession and self-administers the diagnostic test and/or treatment. For example, in some embodiments, at block 311, patient 89 elicits and receives the diagnostic test request from physician 95 via the eye-stimulation electrode system. In some embodiments, at block 321, the diagnostic test is self-administered by patient 89, a data report of the diagnostic test is generated, and the data report is delivered to the patient's/user's physician 95, who, based on the report, at block 97.2 requests a treatment (a treatment that is self-administered by patient 89 as shown at block 341, such as, for example, those treatments described in U.S. Pat. Nos. 10,391,312, 6,035,236, and/or 6,275,735 set forth above). In some embodiments, at block 331, patient 89 elicits and receives the treatment request from the physician 95 via the eye-stimulation electrode system. In some embodiments, block 341 also includes performing a follow-on diagnostic test, such as done at block 321, to see if there are any immediate improved results. In some embodiments, at block 351, the results from the follow-on diagnostic test performed as part of block 341 are checked (in some embodiments, optionally including a review by physician 95), and if appropriate, an approval or rejection (as appropriate) is issued at block 351, and provided to the user/patient 89 and stored in database 360 that maintains a log of patients and results of checkups.

Figure 3C:
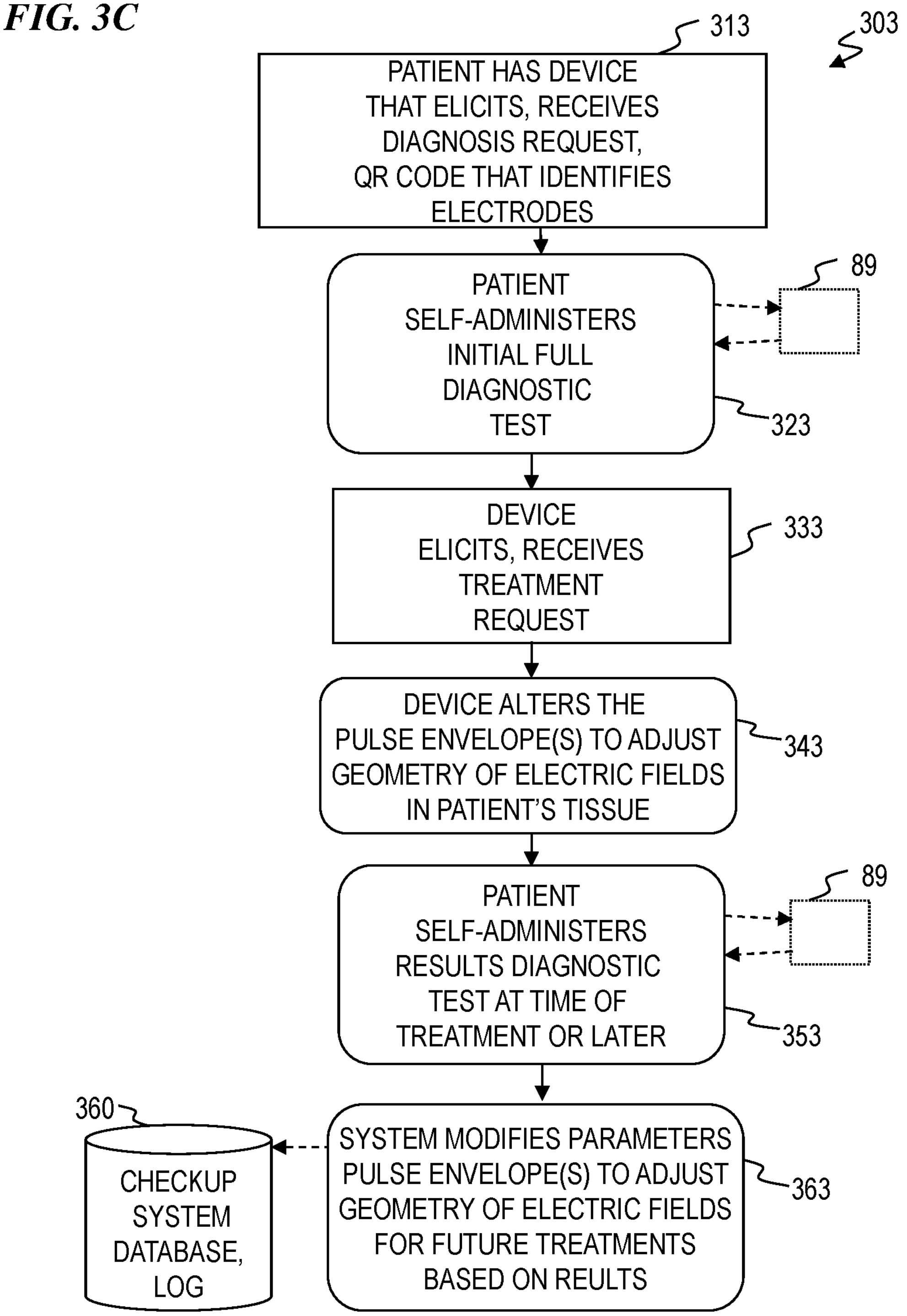
FIG. 3C is a block diagram/flow chart of an eye-stimulation system and method 303 for control of the geometry of electrical stimulation applied to a human eye, according to some embodiments of the present invention.

FIG. 3C is a block diagram/flow chart of an eye-stimulation system and method 303 for control of the geometry of electrical stimulation applied to a human eye, according to some embodiments of the present invention. In some embodiments, as shown in method 303, physician 95 is removed from the process completely and patient 89 self-administers the diagnostic test(s) and/or treatment. For example, in some embodiments, at block 313, patient 89 has the eye-stimulation electrode system in their possession and patient 89 uses the eye-stimulation electrode system and its associated QR code (containing, e.g., the serial number identifying the eye-stimulation electrode system) to submit a diagnosis request. In some embodiments, at block 323, patient 89 self-administers the initial full diagnostic test, a data report of the diagnostic test is generated, and the data report is delivered to patient 89, who, based on the report, at block 333, requests a treatment (a treatment that is self-administered by patient 89 as shown at block 353, such as, for example, those treatments described in U.S. Pat. Nos. 10,391,312, 6,035,236, and/or 6,275,735 set forth above). In some embodiments, at block 343, the eye-stimulation electrode system alters the pulse envelope(s) to adjust the geometry of the electric fields applied to the patient's tissue during the treatment. In some embodiments, at block 353, patient 89 self-administers the treatment, and, in some embodiments, block 353 also includes performing a follow-on diagnostic test, such as done at block 323, to see if there are any immediate improved results. In some embodiments, at block 363, based on the results from the follow-on diagnostic test performed as part of block 353, the eye-stimulation electrode system modifies parameters for pulse envelopes to adjust the geometry of the electric fields applied to patient 89 during future treatments (in some such embodiments, the modified parameters are stored in database 360 that maintains a log of patients and results of checkups).

Figure 4:
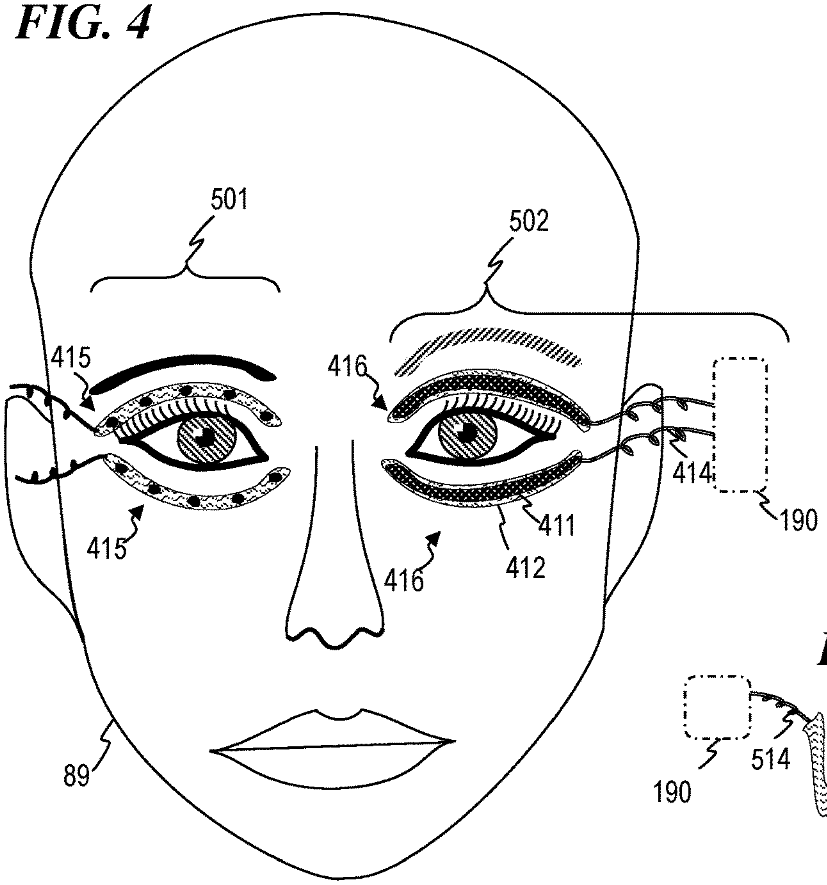
FIG. 4 is a front view of a patient 89 having two different alternative eye-stimulation electrodes 415 and 416 that can be used, along with one or more of the return electrodes shown in FIG. 1A1-1C3, 2A, 2B, 2C, 2E or 2F for control of the geometry of electrical stimulation applied to a human eye, according to some embodiments of the present invention.

FIG. 4 is a front view of a patient 89 having two different alternative eye-stimulation electrodes 415 and 416 that can be used, along with one or more of the return electrodes shown in FIG. 1A1-1C3, 2A, 2B, 2C, 2E or 2F for control of the geometry of electrical stimulation applied to a human eye, according to some embodiments of the present invention. In some embodiments, eye-stimulation electrodes 415 includes a plurality of individually activatable electrodes on the upper eyelid strip and the lower eyelid strip, which are separated and individually applied to the patient's eyelid one at a time. In some embodiments, eye-stimulation electrodes 416 includes a single individually activatable electrode on the upper eyelid strip and another on the lower eyelid strip, which are separated and individually applied to the patient's eyelid one at a time.

Figure 5C:
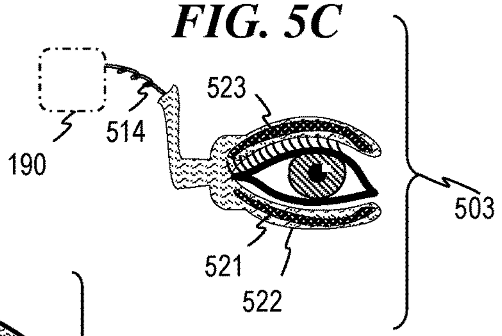
FIG. 5C is a front view of a system 503 using eye-stimulation electrodes 521 and 523 on a single strip 522 that can be used, along with one or more of the return electrodes shown in FIG. 1A1-1C3, 2A, 2B, 2C, 2E or 2F for control of the geometry of electrical stimulation applied to a human eye, according to some embodiments of the present invention.
Figure 5A:
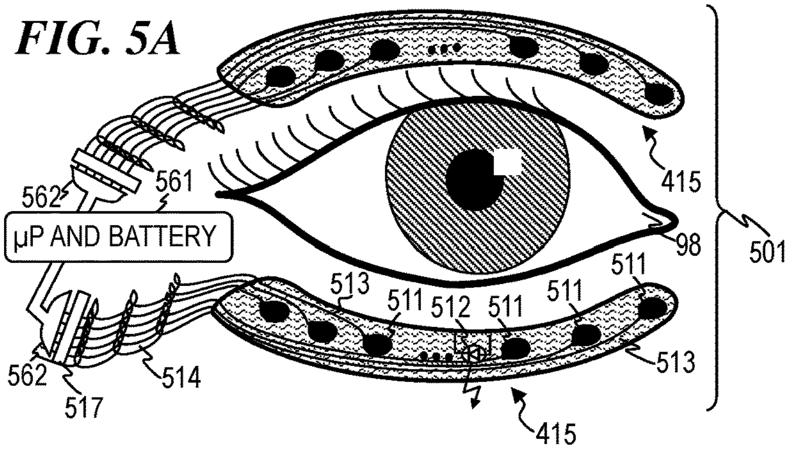
FIG. 5A is a front view of a system 501 using eye-stimulation electrodes 415 that can be used, along with one or more of the return electrodes shown in FIG. 1A1-1C3, 2A, 2B, 2C, 2E or 2F for control of the geometry of electrical stimulation applied to a human eye, according to some embodiments of the present invention.

FIG. 5A is a front view of a system 501 using eye-stimulation electrodes 415 that can be used, along with one or more of the return electrodes shown in FIG. 1A1-1C3, 2A, 2B, 2C, 2E or 2F for control of the geometry of electrical stimulation applied to a human eye, according to some embodiments of the present invention. In some embodiments, system 501 includes one or more strip substrates 512, each substrate 512 having a plurality of electrodes 511. In some embodiments, each of the plurality of electrodes 511 is coupled to a corresponding electrical conductor 513. In some embodiments, system 501 includes a micro-current stimulation controller 561 that is operatively coupled to the plurality of electrodes 511 via electrical conductors 513. In some embodiments, micro-current stimulation controller 561 includes a microprocessor (μP) operated by a battery, and optionally is controlled and/or programmed by a nearby laptop personal computer, a tablet computer, a desktop computer or the like. In some embodiments, each disposable therapy-appliance strip 415 includes a wire bundle 514 (that includes a plurality of the electrical conductors 513) electrically coupled to an electrical connector 517 that plugs into or otherwise electrically connects to a corresponding connector 562 on controller apparatus 561.

Figure 5B:
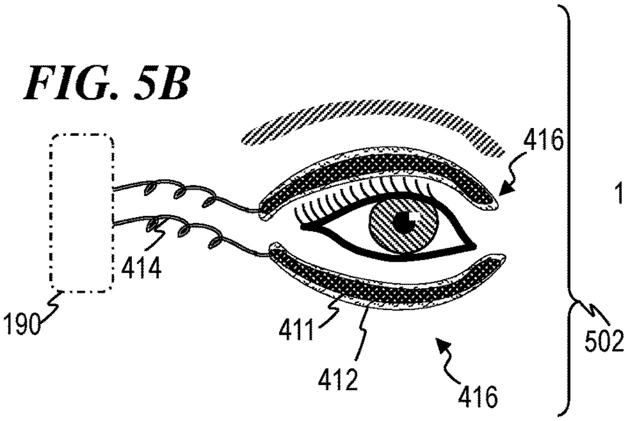
FIG. 5B is a front view of a system 502 using eye-stimulation electrodes 416 that can be used, along with one or more of the return electrodes shown in FIG. 1A1-1C3, 2A, 2B, 2C, 2E or 2F for control of the geometry of electrical stimulation applied to a human eye, according to some embodiments of the present invention.

FIG. 5B is a front view of a system 502 using eye-stimulation electrodes 416 that can be used, along with one or more of the return electrodes shown in FIG. 1A1-1C3, 2A, 2B, 2C, 2E or 2F for control of the geometry of electrical stimulation applied to a human eye, according to some embodiments of the present invention. In some embodiments, system 502 includes a controller 190. In some embodiments, each eye-stimulation electrode 416 includes an electrode 521 deposited as metal layers on a flexible insulating substrate 522, and each electrode 521 is coupled to controller 190 via a corresponding electrical connection 414.

FIG. 5C is a front view of a system 503 using eye-stimulation electrodes 521 and 523 on a single strip 522 that can be used, along with one or more of the return electrodes shown in FIG. 1A1-1C3, 2A, 2B, 2C, 2E or 2F for control of the geometry of electrical stimulation applied to a human eye, according to some embodiments of the present invention. In some embodiments, electrodes 521 and 523 are coupled to controller 190 via a single electrical connection 514.

Figure 5D:
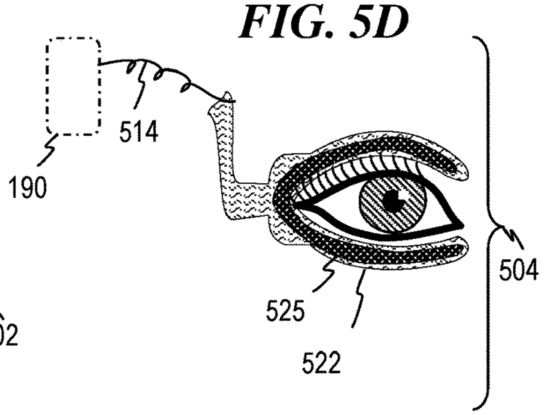
FIG. 5D is a front view of a system 504 using a single wrap-around eye-stimulation electrode 525 that can be used, along with one or more of the return electrodes shown in FIG. 1A1-1C3, 2A, 2B, 2C, 2E or 2F for control of the geometry of electrical stimulation applied to a human eye, according to some embodiments of the present invention.

FIG. 5D is a front view of a system 601 using a single eye-stimulation electrodes 525 on a single strip 522 that can be used, along with one or more of the return electrodes shown in FIG. 1A1-1C3, 2A, 2B, 2C, 2E or 2F for control of the geometry of electrical stimulation applied to a human eye, according to some embodiments of the present invention.

Figure 6A:
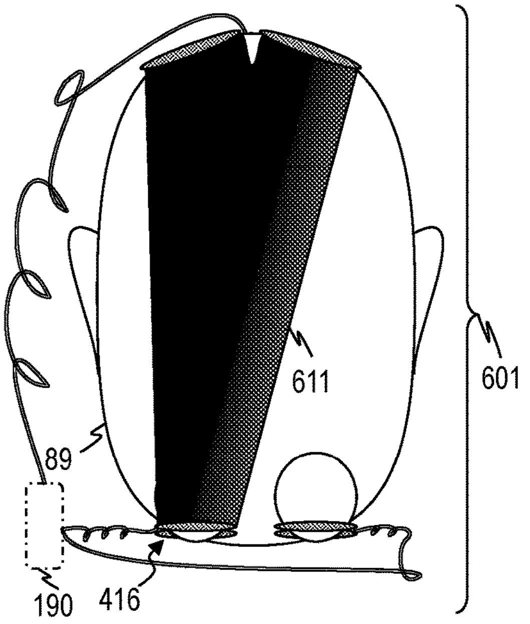
FIG. 6A is a top cross-sectional schematic view of the electric field 611 in the head of a patient 89 with a system configuration 601 using eye-stimulation electrodes that can be used, along with one or more of the sets of return electrodes shown in FIG. 1A1-1C3, 2A, 2B, 2C, 2E or 2F, for control of the geometry of electrical stimulation applied to the left-hand eye, according to some embodiments of the present invention.

FIG. 6A is a top cross-sectional schematic view of the electric field 611 in the head of a patient 89 with a system configuration 601 using eye-stimulation electrodes 416 that can be used, along with one or more of the sets of return electrodes shown in FIG. 1A1-1C3, 2A, 2B, 2C, 2E or 2F, for control of the geometry of electrical stimulation applied to the left-hand eye, according to some embodiments of the present invention. In some embodiments, eye electrodes 416 and the return electrodes are coupled to controller 190.

Figure 6B:
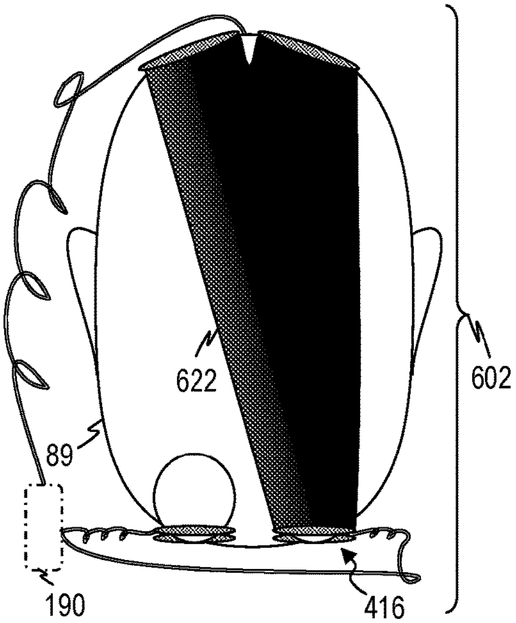
FIG. 6B is a top cross-sectional schematic view of the electric field 622 in the head of a patient 89 with a system configuration 602 for control of the geometry of electrical stimulation applied to the right-hand eye, according to some embodiments of the present invention.

FIG. 6B is a top cross-sectional schematic view of the electric field 622 in the head of a patient 89 with a system configuration 602 for control of the geometry of electrical stimulation applied to the right-hand eye, according to some embodiments of the present invention.

Figure 7A:
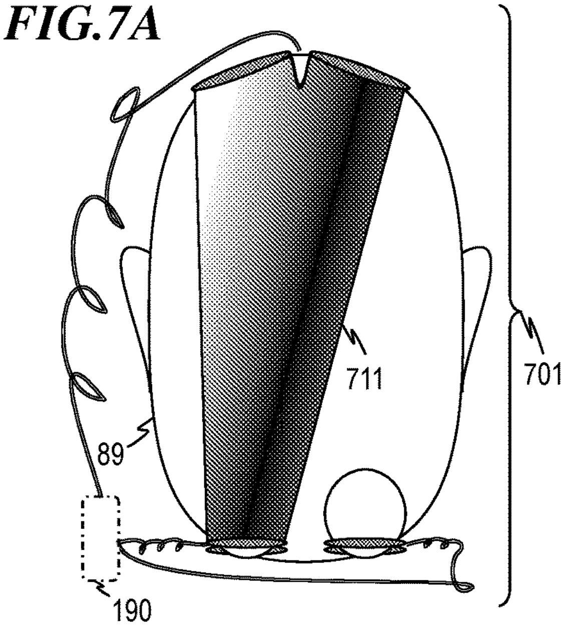
FIG. 7A is a top cross-sectional schematic view of the electric field 711 in the head of a patient 89 with a system configuration 701 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention.

FIG. 7A is a top cross-sectional schematic view of the electric field 711 in the head of a patient 89 with a system configuration 701 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention. In some embodiments, eye electrodes and the return electrodes are coupled to controller 190. In some embodiments, electric field 711 primarily travels from an eye electrode on the right-hand eye to the return electrode on the side of the head opposite the right-hand eye.

Figure 7B:
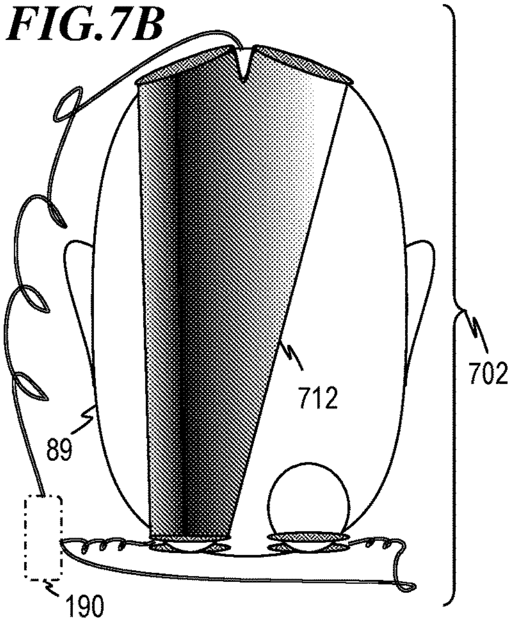
FIG. 7B is a top cross-sectional schematic view of the electric field 712 in the head of a patient 89 with a system configuration 702 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention.

FIG. 7B is a top cross-sectional schematic view of the electric field 712 in the head of a patient 89 with a system configuration 702 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention. In some embodiments, electric field 712 primarily travels from one or more eye electrodes 416 on the right-hand eye to the return electrode on the same side of the head as the right-hand eye.

Figure 7C:
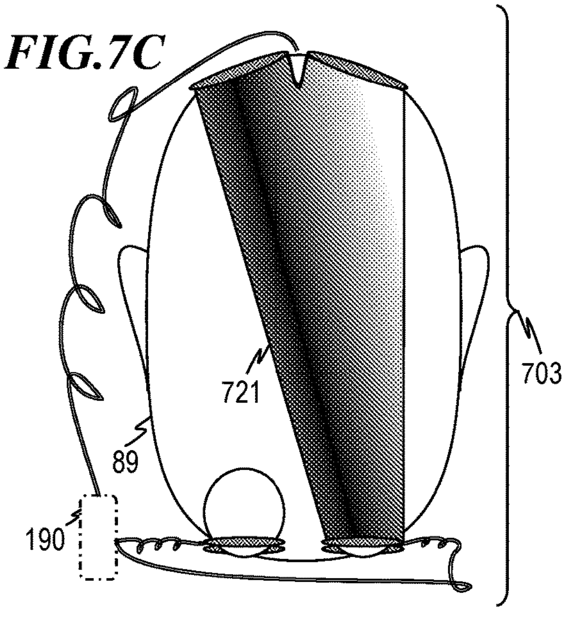
FIG. 7C is a top cross-sectional schematic view of the electric field 721 in the head of a patient 89 with a system configuration 703 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention.

FIG. 7C is a top cross-sectional schematic view of the electric field 721 in the head of a patient 89 with a system configuration 703 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention. In some embodiments, electric field 721 primarily travels from one or more eye electrodes 416 on the left-hand eye to the return electrode on the side of the head opposite the left-hand eye.

Figure 7D:
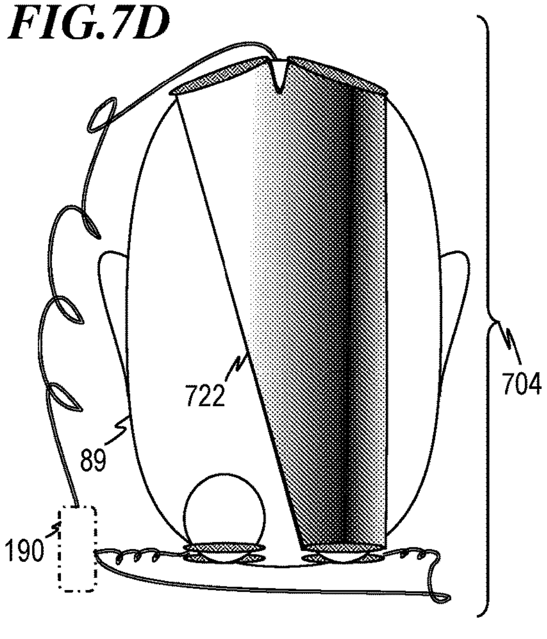
FIG. 7D is a top cross-sectional schematic view of the electric field 722 in the head of a patient 89 with a system configuration 704 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention.

FIG. 7D is a top cross-sectional schematic view of the electric field 722 in the head of a patient 89 with a system configuration 704 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention. In some embodiments, electric field 722 primarily travels from one or more eye electrodes 416 on the left-hand eye to the return electrode on the same side of the head as the left-hand eye.

Figure 7E:
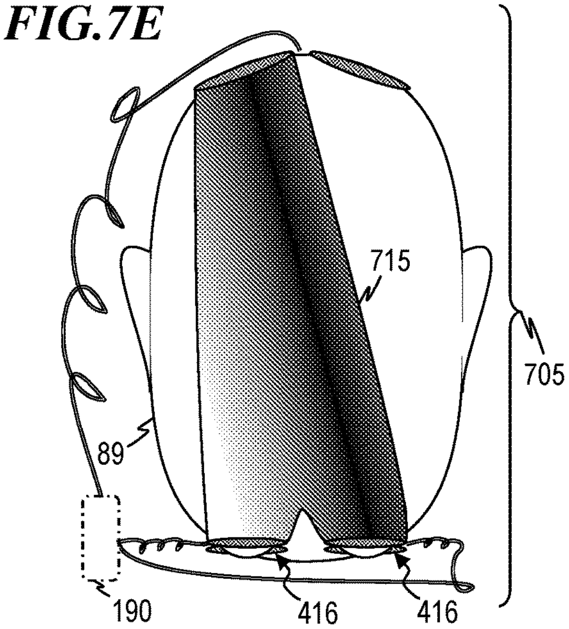
FIG. 7E is a top cross-sectional schematic view of the electric field 715 in the head of a patient 89 with a system configuration 705 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention.

FIG. 7E is a top cross-sectional schematic view of the electric field 715 in the head of a patient 89 with a system configuration 705 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention. In some embodiments, electrodes and the return electrodes are coupled to controller 190. In some embodiments, electric field 715 going from both sets of eye electrodes 416 to the right receiving electrode, primarily travels from electrode on the right eye to the return electrode on the left side of the head.

Figure 7F:
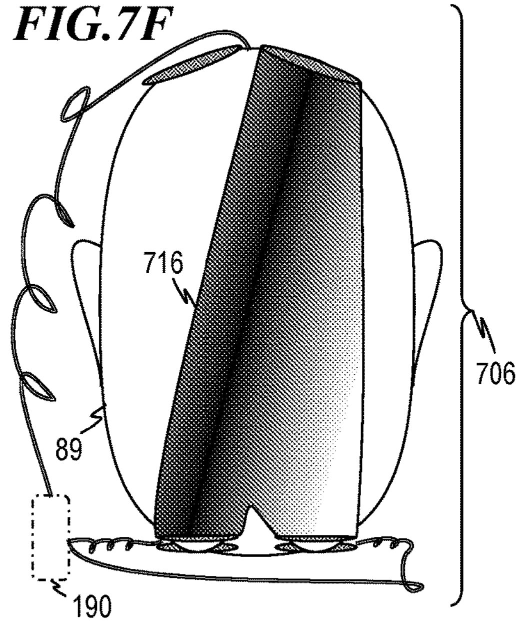
FIG. 7F is a top cross-sectional schematic view of the electric field 716 in the head of a patient 89 with a system configuration 706 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention.

FIG. 7F is a top cross-sectional schematic view of the electric field 716 in the head of a patient 89 with a system configuration 706 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention. In some embodiments, electric field 716 going from both sets of eye electrodes 416 to the left receiving electrode, primarily travels from electrode on the right eye to the return electrode on the left side of the head.

Figure 7G:
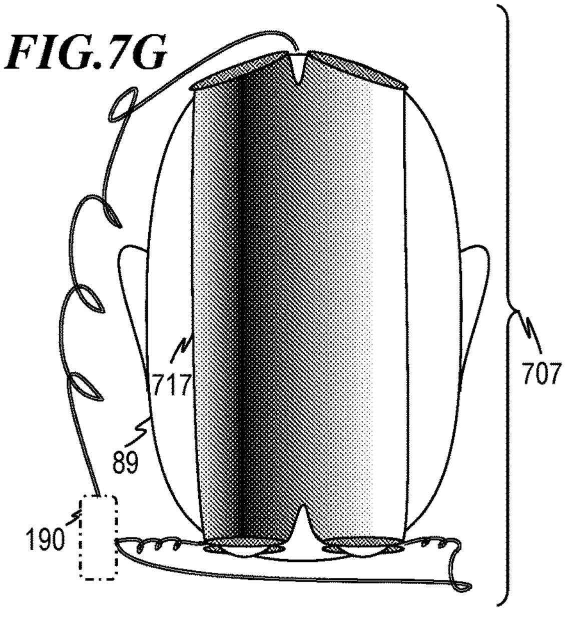
FIG. 7G is a top cross-sectional schematic view of the electric field 717 in the head of a patient 89 with a system configuration 707 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention.

FIG. 7G is a top cross-sectional schematic view of the electric field 717 in the head of a patient 89 with a system configuration 707 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention. In some embodiments, electric field 717 going from both sets of eye electrodes 416 to both sets of receiving electrodes, primarily travels from electrode on the right-hand eye to the return electrode on the same side of the head as the left-hand eye.

Figure 7H:
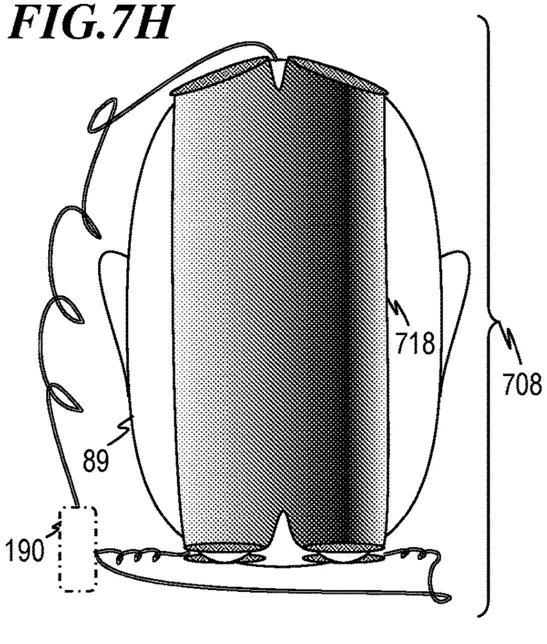
FIG. 7H is a top cross-sectional schematic view of the electric field 718 in the head of a patient 89 with a system configuration 708 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention.

FIG. 7H is a top cross-sectional schematic view of the electric field 718 in the head of a patient 89 with a system configuration 708 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention. In some embodiments, electric field 718 going from both sets of eye electrodes 416 to both sets of receiving electrodes, primarily travels from electrode on the right-hand eye to the return electrode on the same side of the head as the right-hand eye.

Figure 8A:
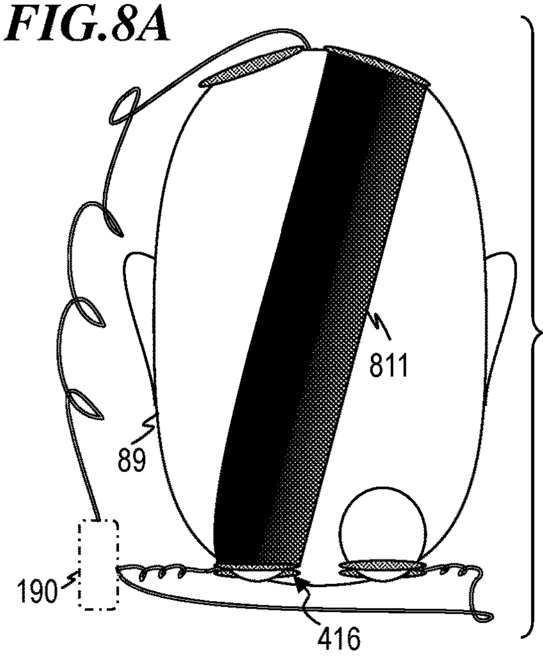
FIG. 8A is a top cross-sectional schematic view of the electric field 811 in the head of a patient 89 with a system configuration 801 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention.

FIG. 8A is a top cross-sectional schematic view of the electric field 811 in the head of a patient 89 with a system configuration 801 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention. In some embodiments, electrodes 416 and the return electrodes are coupled to controller 190. In some embodiments, electric field 811 travels from one or more electrodes 416 on the left-hand eye to the return electrode on the side of the head opposite the left-hand eye.

Figure 8B:
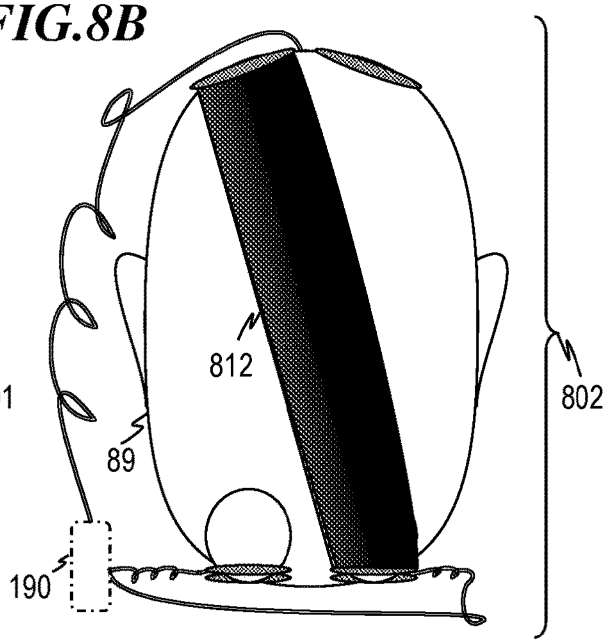
FIG. 8B is a top cross-sectional schematic view of the electric field 812 in the head of a patient 89 with a system configuration 802 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention.

FIG. 8B is a top cross-sectional schematic view of the electric field 812 in the head of a patient 89 with a system configuration 802 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention. In some embodiments, electric field 812 travels from one or more electrodes on the right-hand eye to the return electrode on the side of the head opposite the right-hand eye.

Figure 9A:
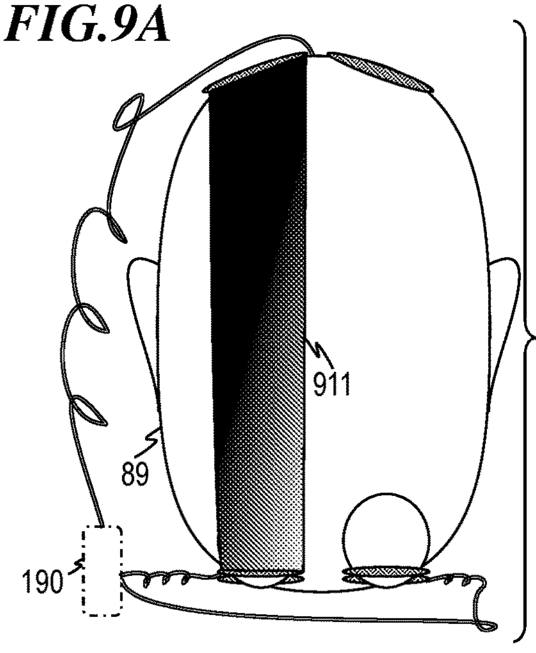
FIG. 9A is a top cross-sectional schematic view of the electric field 911 in the head of a patient 89 with a system configuration 801 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention.

FIG. 9A is a top cross-sectional schematic view of the electric field 911 in the head of a patient 89 with a system configuration 801 using eye-stimulation electrodes that can be used, along with one or more of the sets of return electrodes shown in FIG. 1C1-1C3, 2E or 2F, for control of the geometry of electrical stimulation applied to the left-hand eye, according to some embodiments of the present invention. In some embodiments, electrodes 416 and the return electrodes are coupled to controller 190. In some embodiments, electric field 911 travels from one or more eye electrodes on the left-hand eye to the return electrode on the same side of the head as the left-hand eye.

Figure 9B:
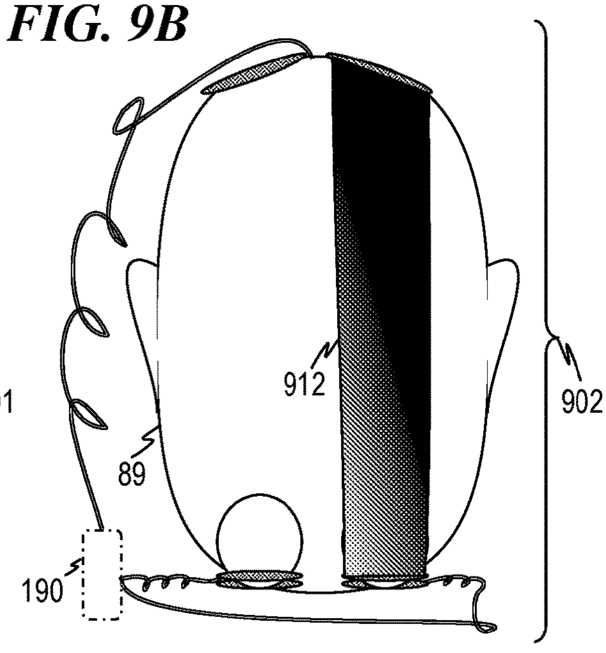
FIG. 9B is a top cross-sectional schematic view of the electric field 912 in the head of a patient 89 with a system configuration 802 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention.

FIG. 9B is a top cross-sectional schematic view of the electric field 912 in the head of a patient 89 with a system configuration 802 using eye-stimulation electrodes that can be used, along with one or more of the sets of return electrodes shown in FIG. 1C1-1C3, 2E or 2F, for control of the geometry of electrical stimulation applied to the right-hand eye, according to some embodiments of the present invention. In some embodiments, electric field 912 travels from one or more eye electrodes on the right-hand eye to the return electrode on the same side of the head as the right-hand eye.

Figure 10A:
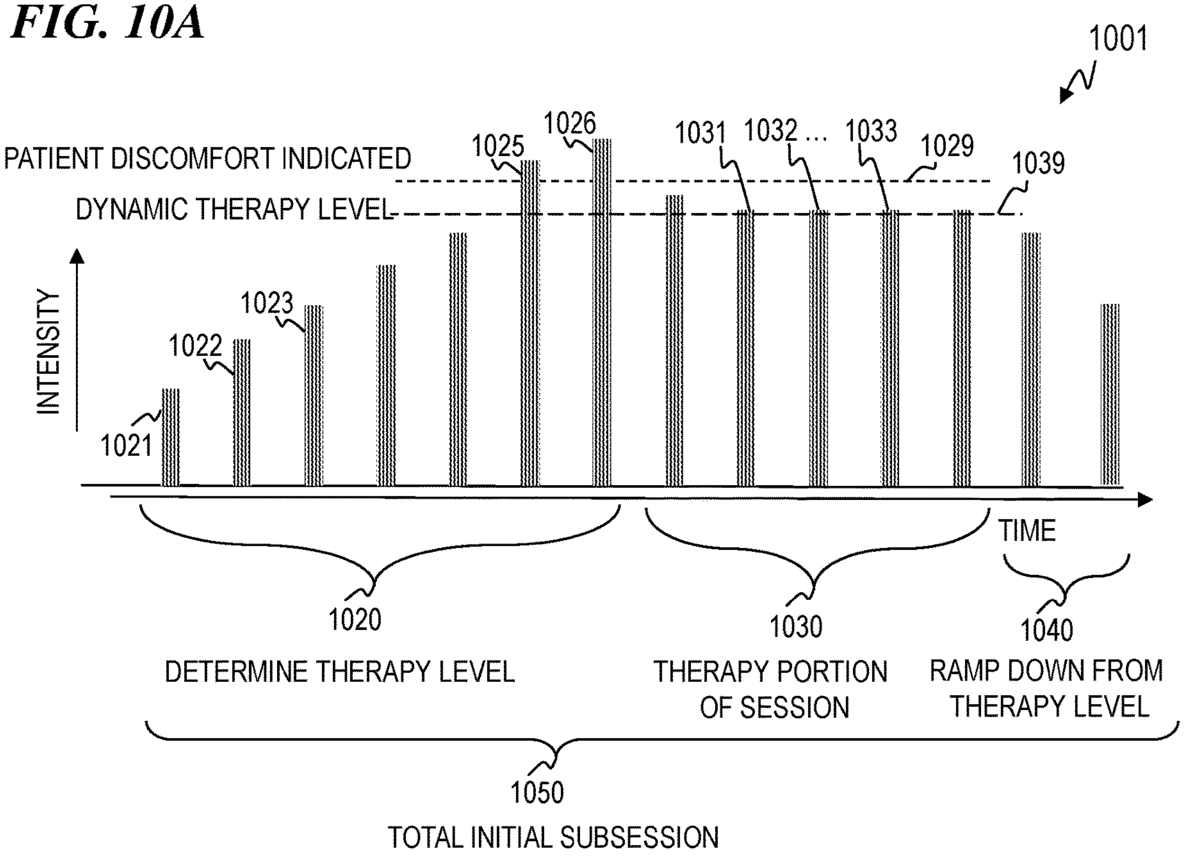
FIG. 10A is a graph 1001 of electrical signal amplitude over time as applied to an eye of a patient during an initial sub-session 1050 used to determine an amplitude of signal that is both effective and not too uncomfortable to the patient, according to some embodiments of the present invention.

FIG. 10A is a graph 1001 of electrical signal amplitude over time as applied to an eye of a patient during an initial sub-session 1050 used to determine an amplitude of signal that is both effective and not too uncomfortable to the patient, according to some embodiments of the present invention. In some embodiments, an intensity-determination series of pulses 1020 are generated that have gradually increasing electrical current amplitude (see pulses 1021, 1022, and 1023, etc.), such that controller 190 (see, e.g., FIG. 2A) receives feedback as to the skin impedance and/or patient-generated feedback (such as a voice command (or shriek) or a push-button switch signal) that indicates patient discomfort (see, e.g., pulses 1025 and 1026 that are above the discomfort level 1029), and upon receiving such feedback signal from the patient or the patient's physiological response to the pulses), controller 190 reduces the current and/or voltage of the pulses to a therapeutic level 1039 that is better tolerated than the level causing discomfort. In some embodiments, a therapy series of pulses 1030 is then applied, e.g., therapy pulses 1031, 1032, 1033, etc. In some embodiments, a ramp-down series of pulses 1040 is applied after the therapy series of pulses 1030. In some embodiments, initial sub-session 1050 includes the intensity-determination series of pulses 1020, the therapy series of pulses 1030, and the ramp-down series of pulses 1040.

Figure 10B:
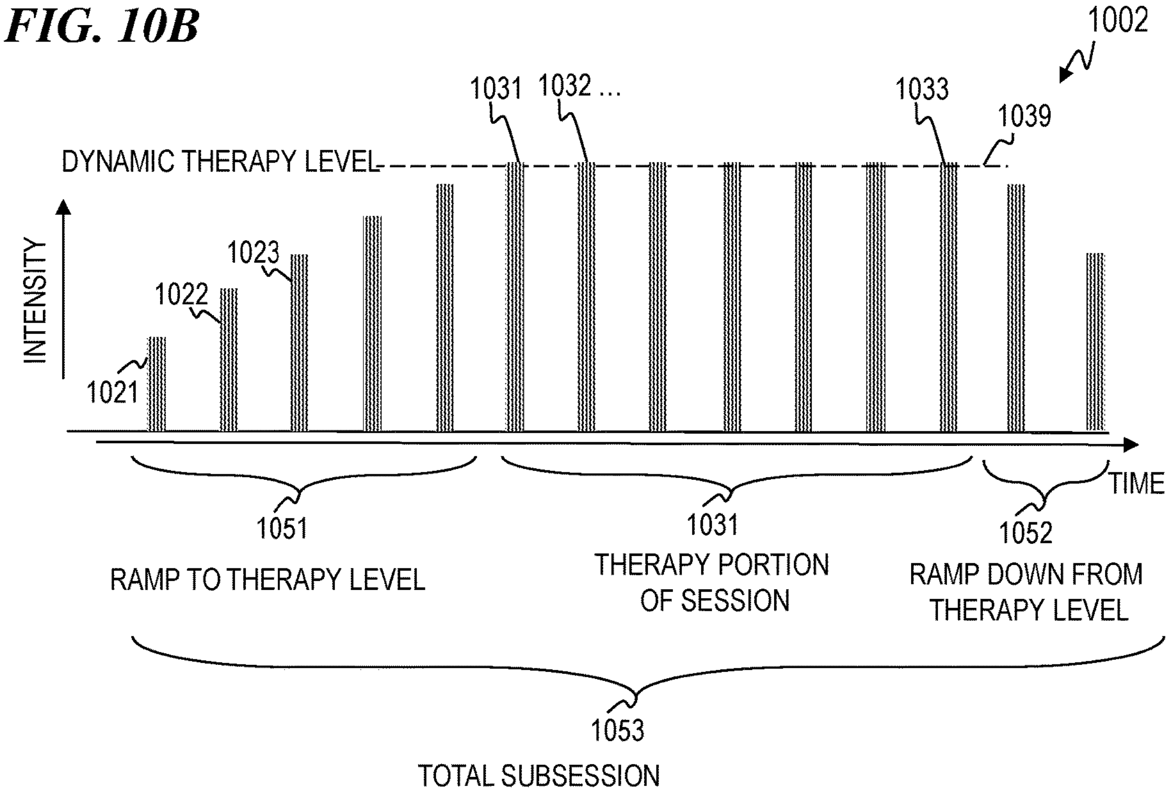
FIG. 10B is a graph 1002 of electrical signal amplitude over time as applied to an eye of a patient during a sub-session 1053, to apply an amplitude of signal that is both effective and not too uncomfortable to the patient, according to some embodiments of the present invention.

FIG. 10B is a graph 1002 of electrical signal amplitude over time as applied to an eye of a patient during a sub-session 1053, to apply an amplitude of signal that is both effective and not too uncomfortable to the patient, according to some embodiments of the present invention. In some embodiments, a ramp-to-therapy-level series of pulses 1051 are generated that gradually increase the electrical current amplitude to the therapeutic level 1039 that is determined during the initial sub-session 1050 of FIG. 10A. In some embodiments, a therapy series of pulses 1031 is then applied, followed by a ramp-down series of pulses 1052. In some embodiments, sub-session 1053 includes the ramp-to-therapy-level series of pulses 1051, the therapy series of pulses 1031, and the ramp-down series of pulses 1052.

FIG. 10C is a block diagram of a system 1003 that can vary amplitude over time of signals as applied to an eye of a patient, such that the amplitude of the signals is both effective and not too uncomfortable to the patient according to some embodiments of the present invention. In some embodiments, system 1003 includes base station 1090, controller 1081, FLASH drive 1096, disposable electrodes 1072, and (as needed) disposable ground patches, conductive gel and cleaning wipes. In some embodiments, base station 1090 is a device, such as a laptop personal computer (PC), tablet computer, desktop computer or the like, for selecting parameters, monitoring performance, data collection and storage and communication with the control unit (controller 1081). In some embodiments, controller 1081 is a control unit that contains the electronics that deliver current to the electrode contacts on the eye. In some embodiments, the electrode contacts are part of a disposable strip, goggles or an individual probe or the like. In some embodiments, FLASH drive 1096 is a USB "thumb drive" that includes encrypted data and program code to provide a fixed number of prepaid patient therapies, wherein each time a successful therapy is completed one therapy unit is deducted from the flash drive. In some embodiments, FLASH drive 1096 is a USB "thumb drive" that includes encrypted data and program code to provide prescriptions for specific patient therapies, wherein each time a successful therapy is completed one therapy unit is deducted from the flash drive. In some embodiments, once all available therapy unit sessions are completed, the FLASH drive 1096 can be discarded and a new prepaid flash drive is used. In other embodiments, the FLASH drive 1096 is also used to gather and record session data and parameters that can be later analyzed to determine long-term effectiveness of various different therapy variations, so once all available therapy unit sessions are completed, the FLASH drive 1096 is returned to the analysis facility and in exchange for the data and a per-therapy-session fee, a new prepaid flash drive is sent out to the treatment facility. In some embodiments, the patient identification data is anonymized and encrypted for patient privacy and/or legal requirements, while keeping each session with enough information to analyze what works and what does not work. In some embodiments, disposable electrodes 1072 include a plurality of electrode contacts in the form of an adhesive strip, disposable handheld probe tip or goggle, that includes, for example, six to twelve contacts (or other suitable number), split with some on the upper eyelid portion and others on the lower eyelid portion. In some embodiments, a kit is provided wherein, in addition to the above-mentioned disposable electrodes 1072 (contact strips), one or more handheld probe tips, and/or goggles and the flash drive, the kit also includes such items as disposable ground patches, conductive gel and cleaning wipes.

In some embodiments, controller 1081 includes a microprocessor 1061, a power system (such as a battery, ultracapacitor or the like) 1062 that supplies electrical power to the rest of the controller 1081, a current-source 1063 that is controlled by microprocessor 1061 based on signals from current and impedance sensor 1069, an electrode sequencer and current balancer 1064 that selects, for example, which two or three of six possible electrodes to which to send the electrical pulse signal at any moment in time, as controlled by microprocessor 1061, and these pulses are sent through electrode connectors 1066 to the set of electrodes 1072. In some embodiments, sequencer and current balancer 1064 also controls/generates a pulse envelope associated with the electrical stimulation treatment. In some embodiments, the set of disposable electrodes 1072 also includes one or more status LEDs 1067 and/or one or more stimulation LEDs 1077 embedded in or on the strip, wherein status LEDs 1067 and stimulation LEDs 1077 are driven by electrical signals sent through connector 1066. In other embodiments, one or more status LEDs 1067 and/or stimulation LEDs 1077 are located in the controller 1081 and emit light directly from controller 1081, and/or through optical fibers 1071 or the like embedded in or on the strip to emission points on the electrode strip, wherein these LEDs 1067 and/or LEDs 1077 are driven by electrical signals from microprocessor 1061. In some embodiments, status LEDs 1067 provide a status and patient-feedback function to tell the medical-professional person and/or the patient that the system is functioning and active. In some embodiments, stimulation LEDs 1077 provide nerve-stimulating light signals that are sufficient (e.g., infrared light signals with a sufficiently high intensity) to generate a nerve-action potential (NAP) in the target tissue of patient 89. In some embodiments, the electric field provided by electrodes 1072 acts as a preconditioner for the nerve-stimulating light signals generated by LEDs 1077 such that a NAP is generated by the nerve-stimulating light signals at an intensity that is lower than would have been required if no electric field was provided.

In some embodiments, a wireless communications device 1068 (such as Bluetooth® NFC, infrared optical communications, or the like) provides one-way or two-way communications to a base station 1090. In some embodiments, base station 1090, based on a prepaid therapy authorization from, e.g., FLASH drive 1096, transmits 1091 programming information specific for the particular patient, wherein the authorization optionally includes authorization based on a fee having been paid, as well as patient-specific therapy control information that has been customized for the particular identified patient to be treated this session based on a treatment regimen prescribed by an eye doctor or the like. In some embodiments, session parameters are communicated 1092 back to the base station 1090 (with parameters such as the actual number, polarity, sequence and strength of pulses, the measured impedance and/or current, indicated patient discomfort, and the like). In some embodiments, system 1003 includes a patient-activatable switch (e.g., on controller 1081 or via a separate handheld switch that is wirelessly or in wired communication with controller 1081) that the patient is instructed to press if and when the patient feels discomfort or concern, and upon activation of that switch, electrical output from controller 1081 or even the entire controller 1081 is immediately shut off, and/or the timing of the activation of the switch by the patient is recorded and transmitted in the communication 1092 of parameters from the session. Thus, this feedback from the patient herself or himself, in some embodiments, is used to fully shut down the device (for patient comfort and peace-of-mind, as well as a further enhancement to patient safety just in case the current source 1063 has a fault and is sending too much current), and is then correlated to a particular time or other aspect of the treatment to allow design of better therapy sessions in the future, and/or can be used to immediately terminate the session (wherein microcontroller 1061 will immediately change all connections to "OFF" (or high impedance) to block any further current to the patient, and/or the entire controller 1081 is then (i.e., after storing the timestamp of the switch press by the patient) shut down and disconnected from power source (e.g., battery) 1062. In some embodiments, controller 1081 and/or base station 1090 include an audio/vibration-output unit 1070 that provides a sound (beep, chime, ding, or the like) and/or vibration associated with therapy session status, to indicate, e.g., "ON/session starting," in therapy, an alert as to insufficient or inappropriate treatment, and "OFF/session ending."

In some embodiments, system 1003 is a software-driven system that provides programmability of all parameters including frequency, waveform, current level, duration of therapy and number of "cycles" around the eye (wherein, in some embodiments, one cycle is the independent activation of each of the six to twelve electrode contacts). In some embodiments, these parameters are programmed during manufacturing, while in other embodiments, the parameters are programmed in the field by the clinician or a company representative. In some embodiments, modifications to the programming parameters and/or software (e.g., as customized by the prescription for the treatment protocol provided by a licensed medical professional for a specific identified patient) are stored in a plug-in storage device 1096 (such as a USB FLASH storage device or the like) and the parameters and/or program and loaded (by plugging-in device 1096) into base station 1090 (and then transmitted 1091 (e.g., wirelessly or by wired connection) to controller 1081 to be stored in the memory of microprocessor 1061). In other embodiments, plug-in storage device 1096 is plugged directly into controller 701 to load and store the parameters and/or program into the memory of microprocessor 1061 (in some such embodiments, the base station 1090 is omitted, while in other embodiments, base station 1090 is retained to provide the technician/medical professional with status of each session in real time). In some embodiments, base station 1090 is used to provide the technician/medical professional with status of each session of a plurality of simultaneous patient sessions in real time (e.g., in some embodiments, a laptop computer used as base station 1090 is programmed to provide a split-screen progress monitor (e.g., wherein the display screen is split into, e.g., quadrants if up to four patients were simultaneously treated) for a plurality of treatment sessions for each of a plurality of patients). In some embodiments, the software may also be modified remotely using the wireless connection to the base station 1090. In some embodiments, a prescription for a treatment session (the protocol, parameters and the like for controlling current amount, pulse duration, inter-pulse spacing and how many pulses are to be sent and the like) for each individual patient is prepared and checked by a licensed professional, and this prescription is downloaded and/or stored in base station 1090, or into USB device 1096 along with the prepaid activation code to enable only authorized treatments for specific patients. In some embodiments, the software in base station 1090 and/or the software in controller 1081 verifies the match between a specific patient's prescription associated with a specific identified patient and patient-identification information of the specific identified patient in order to verify that the correct prescription is used for that patient.

Some embodiments include a large memory in the controller 1081 and/or in the base station 1090 to capture and record all pertinent patient and clinic data, including the treatment protocol such as the number of pulses applied to each electrode, the amount of current, and all other relevant parameters of what the treatment session involved (including, for example, whether an actual or sham treatment session was provided to the particular patient). In some embodiments, the recorded data are stored in a permanent-memory portion of USB storage device 1096 (e.g., using a portion of memory that allows only a single write operation that may be followed by many read operations, in order that the data are permanently stored and later available). In some embodiments, these data are collected remotely and summarized by company and/or clinic personnel. In some embodiments, data is summarized to provide comparisons between patients and clinics and may be used in research. Over time, this data will allow the company or analysis facility to optimize the design and the clinical protocol, thus improving outcomes.

Some embodiments provide greater current-drive capacity via current source 1063, as well as better current and impedance measurements via sensor unit 1069. This allows the controller 1081 to deliver greater, and more-carefully controlled, current levels that overcome any unexpected higher impedance levels. In some embodiments, system 1003 has a governor (e.g., current controller) to prevent delivery of more than 350 microamps (μA) to the patient during therapy. In some embodiments, base station 1090 and/or controller 1081 may be activated only via an appropriately encoded message from flash drive 1096, or via an authentic encrypted code (e.g., in some embodiments, received from a company website on the internet) that enables the laptop to signal, via WI-FI in some embodiments, the microstimulation controller 1061 to conduct the therapy session for a particular identified patient. In some embodiments, the microstimulation controller 1061 and controller 1081 is implemented on the goggle 1095, and controller 1081 may be activated via a flash drive 1096 plugged into controller 1081 or by any other suitable type of connection (such as a USB cable to base station 1090).

Some embodiments provide automatic adjustment to changes in impedance. As impedance changes during treatment, from contact to contact and from eye to eye, the control unit 1081 will automatically adjust to maintain a consistent current level. This improves performance and outcomes. The treatment has been automated to minimize clinician involvement. The system 1003 automatically manages the therapy to ensure uniform and repeatable results.

In some embodiments, the control unit 1081 is designed to fit and connect nicely on the left and right ground patches. This eliminates the potential of losing signal to the left and right set of contacts due to patient movement during therapy. The small size of the control unit reduces clutter, improves patient comfort, and improves device consistency and compliance. In some embodiments, the control unit 1081 is designed to be tamper proof (both physically and electronically), and to provide encryption on the programming and the sensed parameters to prevent hacking.

In some embodiments, the base station 1090 communicates with the control unit 1081 via a wireless connection eliminating the need to tether the patient to the base station. This improves compliance and makes the setup and therapy session easier to manage. In some embodiments, the base station 1090 can communicate with multiple control units at one time reducing the number of base stations required, therefore reducing set-up time and the clinician's time to manage multiple patients.

In some embodiments, multiple levels of protection help ensure that the electrical current delivered to the contacts cannot exceed the programmed current. The design ensures that an unsafe level of current cannot be achieved even if the output was shorted (zero impedance). In some embodiments, the control unit 1081 is powered by a small direct-current (DC) button cell and is not connected to the base station during therapy, reducing or eliminating the possibility of injury to the patient. In some embodiments, the low cost of the design allows most or all of the system to be single-use and disposable. In some embodiments, the base station 1090 can communicate with a device such as a goggle device and or strips partially or completely encircling the upper and or lower eyelids, as well as other body parts.

In some embodiments, the present invention provides an apparatus that includes: an electrode system for use in electrical-stimulation treatment, testing and monitoring of vision problems of eyes of a patient, the electrode system including: a plurality of eyelid electrodes configured to applied to eyelids of the patient, and one or more return electrodes configured to applied to a rear portion of the patient's head to facilitate adjustment of the geometry of signal flow through the tissues of the patient. Some embodiments further include an electrical controller operatively coupled to the plurality of eyelid electrodes and to the one or more return electrodes, and configured to vary amounts and polarities of electrical currents applied through each one of the plurality of eyelid electrodes and to the one or more return electrodes at different times so as to vary a geometry of electric fields through the eyes of the patient.

In some embodiments, the present invention provides a system for monitoring vision characteristics of an eye of a patient, wherein the system includes an application that executes on a personal electronic device, wherein the personal electronic device includes a processor, a memory operatively coupled to the processor, and a user interface operatively coupled to the processor. The application includes: an output driver that executes on the processor and causes output of a transient light pattern to an eye of a patient; a response unit that executes on the processor and is configured to elicit and receive an indication of a response of the patient to a perception by the patient of the visually perceptible light pattern; an assessment module that executes on the processor, wherein the assessment module is configured to perform a first vision analysis on the eye of the patient at a first temporal moment in order to produce a first vision-characteristic result, wherein the assessment module is further configured to perform the first vision analysis on the eye of the patient at a second temporal moment in order to produce a second vision-characteristic result, wherein the assessment module is further configured to store the first vision-characteristic result and the second vision-characteristic result in the memory, and wherein the assessment module is further configured to perform a first comparison between the first vision-characteristic result and the second vision-characteristic result, and wherein the user interface is configured to output a first message based at least in part on the first comparison.

Some embodiments further include the processor, the memory operatively coupled to the processor, and the user interface.

In some embodiments, the message is a diagnosis of an eye malady of the patient.

In some embodiments, the message is an indication of a change in relative to a prior diagnosis of an eye malady of the patient.

In some embodiments of the system, the assessment module is further configured to perform a second vision analysis on the eye of the patient at a third time in order to produce a third vision-characteristic result, wherein the assessment module is further configured to perform the second vision analysis on the eye of the patient at a fourth time in order to produce a fourth vision-characteristic result, wherein the third vision-characteristic result and the fourth vision-characteristic result are stored in the memory, wherein the assessment module is further configured to perform a second comparison between the third vision-characteristic result and the fourth vision-characteristic result, and wherein the user interface is configured to generate a second message for the patient based at least in part on the second comparison.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:

an electrode system for use in electrical-stimulation treatment, testing and monitoring of vision problems of eyes of a patient, the electrode system including:

one or more eyelid electrodes configured to be applied to one or more eyelids of the patient, and a plurality of skin-contact return-electrode areas on a single, unitary insulating polymer substrate, wherein the plurality of return-electrode areas is configured to be applied to a rear portion of the patient's head; and an electrical controller operatively coupled to the one or more eyelid electrodes and to the plurality of skin-contact return-electrode areas, and configured to control electrical currents applied through each one of the one or more eyelid electrodes and to the skin-contact return-electrode areas so as to selectively alter a geometry of electric fields through the eyes of the patient.

2. The apparatus of claim 1, wherein the one or more eyelid electrodes include a first eyelid electrode on a first substrate strip configured to be applied to a first eyelid of a first eye of the patient and a second eyelid electrode on a second substrate strip configured to be applied to a first eyelid of a second eye of the patient.

3. The apparatus of claim 1, wherein the electrical controller is further configured to selectively alter the geometry of the electric fields through the eyes of the patient over a plurality of times during a single treatment session.

4. The apparatus of claim 1, wherein the plurality of skin-contact return-electrode areas are electrically connected to each other via an electrically conductive bridge.

5. The apparatus of claim 1, wherein the plurality of skin-contact return-electrode areas includes a first return-electrode area and a second return-electrode area, wherein the first return-electrode area is electrically isolated from the second return-electrode area, and wherein both the first return-electrode area and the second return-electrode area are driven with individually controlled signals from the electrical controller.

6. The apparatus of claim 1, wherein the plurality of skin-contact return-electrode areas includes a first return-electrode area placed on a first side of the rear portion of the patient's head across from a first eye of the patient, and a second return-electrode area placed on a second side of the rear portion of the patient's head across from a second eye of the patient, and wherein the electrical controller is further configured to control the electrical currents applied through each one of the one or more eyelid electrodes and to the plurality of skin-contact return-electrode areas so as to generate a first electric field that passes through the first eye of the patient and to both the first and second return-electrode areas.

7. The apparatus of claim 1, wherein the plurality of skin-contact return-electrode areas includes a first return-electrode area placed on a first side of the rear portion of the patient's head across from a first eye of the patient, and a second return-electrode area placed on a second side of the rear portion of the patient's head across from a second eye of the patient, and wherein the electrical controller is further configured to control the electrical currents applied through each one of the one or more eyelid electrodes and to the plurality of skin-contact return-electrode areas so as to generate a first electric field that passes through the first and second eye of the patient and to the first return-electrode area.

8. The apparatus of claim 1, wherein the plurality of skin-contact return-electrode areas includes a first return-electrode area placed on a first side of the rear portion of the patient's head across from a first eye of the patient, and a second return-electrode area placed on a second side of the rear portion of the patient's head across from a second eye of the patient, and wherein the electrical controller is further configured to control the electrical currents applied through each one of the one or more eyelid electrodes and to the plurality of skin-contact return-electrode areas so as to generate a first electric field that passes through the first eye of the patient and to the second return-electrode area.

9. The apparatus of claim 1, wherein the plurality of skin-contact return-electrode areas includes a first return-electrode area placed on a first side of the rear portion of the patient's head across from a first eye of the patient, and a second return-electrode area placed on a second side of the rear portion of the patient's head across from a second eye of the patient, and wherein the electrical controller is further configured to control the electrical currents applied through each one of the one or more eyelid electrodes and to the plurality of skin-contact return-electrode areas so as to generate a first electric field that passes through the first eye of the patient and to the first return-electrode area.

10. The apparatus of claim 1, wherein the plurality of skin-contact return-electrode areas are separated by an insulating region.

11. The apparatus of claim 10, wherein the insulating polymer substrate includes a pressure-sensitive adhesive for attaching the substrate to the patient's skin.

12. A method for treating eyes of a patient, the method comprising:

providing an electrode system that includes:

one or more eyelid electrodes, and a plurality of skin-contact return-electrode areas on a single, unitary insulating polymer substrate;

applying the one or more eyelid electrodes to one or more eyelids of the patient;

applying the plurality of skin-contact return-electrode areas to a rear portion of the patient's head; and controlling electrical currents applied through each of one of the one or more eyelid electrodes and to the plurality of skin-contact return-electrode areas in order to alter a geometry of electric fields through the eyes of the patient.

13. The method of claim 12, wherein the applying of the plurality of skin-contact return-electrode areas includes: placing a first return-electrode area on a first side of the rear portion of the patient's head across from a first eye of the patient, and placing a second return-electrode area on a second side of the rear portion of the patient's head across from a second eye of the patient; wherein the controlling of the electrical currents includes generating a first electric field that passes through the first eye of the patient and to both the first and second return-electrode areas.

14. The method of claim 12, wherein the applying of the plurality of skin-contact return-electrode areas includes: placing a first return-electrode area on a first side of the rear portion of the patient's head across from a first eye of the patient, and placing a second return-electrode area on a second side of the rear portion of the patient's head across from a second eye of the patient; wherein the controlling of the electrical currents includes generating a first electric field that passes through the first and second eye of the patient and to the first return-electrode area.

15. The method of claim 12, wherein the applying of the plurality of skin-contact return-electrode areas includes: placing a first return-electrode area on a first side of the rear portion of the patient's head across from a first eye of the patient, and placing a second return-electrode area on a second side of the rear portion of the patient's head across from a second eye of the patient; wherein the controlling of the electrical currents includes generating a first electric field that passes through the first eye of the patient and to the second return-electrode area.

16. The method of claim 12, wherein the applying of the plurality of skin-contact return-electrode areas includes: placing a first return-electrode area on a first side of the rear portion of the patient's head across from a first eye of the patient, and placing a second return-electrode area on a second side of the rear portion of the patient's head across from a second eye of the patient; wherein the controlling of the electrical currents includes generating a first electric field that passes through the first eye of the patient and to the first return-electrode area.

17. The method of claim 12, further comprising: electrically connecting the plurality of skin-contact return-electrode areas to each other via an electrically conductive bridge.

18. The method of claim 12, wherein the plurality of skin-contact return-electrode areas includes a first return-electrode area and a second return-electrode area, the method further comprising: electrically isolating the first return-electrode area from the second return-electrode area, wherein the controlling of the electrical currents includes driving both the first return-electrode area and the second return-electrode area with individually controlled signals.

19. The method of claim 12, wherein the plurality of skin-contact return-electrode areas are separated by an insulating region.

20. The method of claim 19, wherein the insulating polymer substrate includes a pressure-sensitive adhesive for attaching the substrate to the patient's skin.

21. An apparatus comprising:

an electrode system for use in electrical-stimulation treatment, testing and monitoring of vision problems of eyes of a patient, the electrode system including:

one or more eyelid electrodes configured to be applied to one or more eyelids of the patient, and a plurality of skin-contact return-electrode areas on a single, unitary insulating polymer substrate, wherein the plurality of return-electrode areas is configured to be applied to a location on the patient's skin other than the one or more eyelids of the patient; and one or more electrical controllers operatively coupled to the one or more eyelid electrodes and to the plurality of skin-contact return-electrode areas, and configured to control electrical currents applied through each one of the one or more eyelid electrodes and to the skin-contact return-electrode areas so as to selectively alter a geometry of electric fields through the eyes of the patient.

* * * * *